United States Patent
Li

(10) Patent No.: US 11,291,796 B2
(45) Date of Patent: Apr. 5, 2022

(54) METHOD AND APPARATUS FOR ADJUSTING USER EMOTION

(71) Applicant: Huawei Technologies Co., Ltd., Shenzhen (CN)

(72) Inventor: Haoran Li, Beijing (CN)

(73) Assignee: Huawei Technologies Co., Ltd, Shenzhen (CN)

( * ) Notice: Subject to any disclaimer, the term of this patent is extended or adjusted under 35 U.S.C. 154(b) by 303 days.

(21) Appl. No.: 16/473,946

(22) PCT Filed: Dec. 29, 2016

(86) PCT No.: PCT/CN2016/113149
§ 371 (c)(1),
(2) Date: Jun. 26, 2019

(87) PCT Pub. No.: WO2018/119924
PCT Pub. Date: Jul. 5, 2018

(65) Prior Publication Data
US 2019/0336724 A1 Nov. 7, 2019

(51) Int. Cl.
*A61M 21/02* (2006.01)
*A61B 5/16* (2006.01)
*G06K 9/00* (2006.01)
*A61B 5/0205* (2006.01)
*A61B 5/00* (2006.01)
(Continued)

(52) U.S. Cl.
CPC .......... *A61M 21/02* (2013.01); *A61B 5/0205* (2013.01); *A61B 5/165* (2013.01); *A61B 5/4803* (2013.01); *A61B 5/486* (2013.01); *A61B 5/741* (2013.01); *A61B 5/742* (2013.01);
*G06K 9/00302* (2013.01); *H04B 1/385* (2013.01); *H04M 1/72448* (2021.01); *A61B 5/021* (2013.01); *A61B 5/024* (2013.01); *A61M 2021/005* (2013.01); *A61M 2021/0027* (2013.01); *A61M 2205/3584* (2013.01); *A61M 2205/50* (2013.01);
(Continued)

(58) Field of Classification Search
CPC .......... A61B 5/165–167; A61B 5/0205; A61B 5/4803; A61B 5/486; A61B 5/021; A61B 5/024; G06F 2203/011; G06K 9/00302; A61M 21/00–02
See application file for complete search history.

(56) References Cited

U.S. PATENT DOCUMENTS

2012/0011477 A1 1/2012 Sivadas
2017/0143246 A1* 5/2017 Flickinger ............ A61B 5/6826
2017/0357969 A1 12/2017 Huang et al.

FOREIGN PATENT DOCUMENTS

CN 101337103 A 1/2009
CN 101437079 A 5/2009
(Continued)

*Primary Examiner* — Thaddeus B Cox
(74) *Attorney, Agent, or Firm* — Slater Matsil, LLP

(57) ABSTRACT

A method and an apparatus for adjusting a user emotion are provided. In one example, the method includes obtaining, by a terminal device, data that represents a physical condition of a user, where the data comprises first data, and the first data is at least one parameter value detected for the user by a wearable device connected to the terminal device. The method also includes obtaining, by the terminal device, emotion information determined based on the data and performing, by the terminal device, an operation corresponding to the emotion information.

20 Claims, 16 Drawing Sheets

S301
A smartphone 300 obtains data that is used to represent a user physical condition S302
The smartphone 300 obtains emotion information determined based on the data S303
The smartphone 300 performs an operation that is corresponding to the emotion information and that is used to adjust the user emotion

(51) Int. Cl.
*H04B 1/3827* (2015.01)
*H04M 1/72448* (2021.01)
*A61B 5/021* (2006.01)
*A61B 5/024* (2006.01)
*A61M 21/00* (2006.01)

(52) U.S. Cl.
CPC ..... *A61M 2205/52* (2013.01); *A61M 2230/06* (2013.01); *A61M 2230/30* (2013.01)

(56) References Cited

FOREIGN PATENT DOCUMENTS

| | | |
|---|---|---|
| CN | 102929660 A | 2/2013 |
| CN | 102986201 A | 3/2013 |
| CN | 104574088 A | 4/2015 |
| CN | 204950975 U | 1/2016 |
| CN | 105607822 A | 5/2016 |
| CN | 105615901 A | 6/2016 |
| CN | 105726045 A | 7/2016 |
| CN | 105871696 A | 8/2016 |
| CN | 106037635 A | 10/2016 |
| CN | 106202860 A | 12/2016 |

* cited by examiner

METHOD AND APPARATUS FOR ADJUSTING USER EMOTION

CROSS-REFERENCE TO RELATED APPLICATIONS

This application is a 371 application of PCT Application No. PCT/CN2016/113149, filed on Dec. 29, 2016, which application is hereby incorporated herein by reference.

TECHNICAL FIELD

This application relates to the field of information technologies, and in particular, to a method and an apparatus for adjusting a user emotion.

BACKGROUND

With acceleration of the pace of life, people's emotions are more fluctuant. The emotions greatly affect both life and work efficiency of people. Therefore, an effective method is needed to adjust people's emotions at any time.

Currently, there is no convenient and effective method for adjusting people's emotions.

SUMMARY

Embodiments of this application provide a method and an apparatus for adjusting a user emotion, so as to adjust people's emotions in a convenient and effective way.

According to a first aspect, an embodiment of this application provides a method for adjusting a user emotion, including: obtaining, by the terminal device, data that is used to represent a user physical condition, where the data that is used to represent the user physical condition includes first data, the first data is at least one parameter value detected for the user by a wearable device connected to the terminal device, and the first data may include at least one of the following parameter values: a pulse intensity, a heart rate value, a blood pressure value, and the like; obtaining, by the terminal device, emotion information determined based on the data; and performing, by the terminal device, an operation that is corresponding to the emotion information and that is used to adjust the user emotion.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

In a possible design, second data detected by the terminal device may be further obtained to improve accuracy of the determined user emotion. Therefore, the data that is obtained by the terminal device and that is used to represent the user physical condition may further include the second data, and the second data is at least one parameter value of the user detected by the terminal device; where the obtaining, by the terminal device, emotion information determined based on the data may be specifically implemented in the following manner: obtaining, by the terminal device, emotion information determined based on the first data and the second data.

In the foregoing design, the emotion is determined by using the wearable device and the two types of data detected by the terminal device, and accuracy of the determining is improved.

In a possible design, the terminal device may determine the emotion information, and the obtaining, by the terminal device, the emotion information determined based on the data may be implemented by determining, by the terminal device, the emotion information based on a parameter value of each parameter in the data and a corresponding weight.

A weight corresponding to each parameter may be stored in a user parameter table. Specifically, the terminal device obtains a weight corresponding to each of the at least one parameter by searching the user parameter table, and separately multiplies a parameter value corresponding to each parameter by a weight corresponding to each parameter for summation, so as to obtain an emotion value of the user; and the terminal device generates the emotion information based on the emotion value.

The user parameter table may be pre-configured on the terminal device, or may be sent by the server.

In a possible design, the server may determine the emotion information, and the obtaining, by the terminal device, emotion information determined based on the data may be implemented by sending, by the terminal device, the obtained data that is used to represent the user physical condition to the server, and receiving the emotion information returned by the server based on the data.

Specifically, when determining the emotion information, the server may generate the emotion information based on a user parameter table and the data, and then send the emotion information to the terminal device, so that the terminal device receives the emotion information sent by the server.

The user parameter table may be obtained after data that is used to represent the user physical condition, that is sent by the terminal device, and that is received by the server in a first set time period closest to a time point at which the data is currently received and the emotion information corresponding to the data that is used to represent the user physical condition and that is confirmed by the user are updated.

In the foregoing design, the emotion information is determined by the server. This can reduce an occupied computing resource of the terminal device, and improve operation efficiency. In addition, in the prior art, a fixed parameter table is usually used to determine an emotion, and a difference between users is not considered, for example, a user has a relatively high heart rate, but another user has a relatively low heart rate. In this embodiment of this application, an artificial intelligence algorithm is used to update the parameter weight, so as to improve emotion determining accuracy.

In a possible design, the performing, by the terminal device, an operation that is corresponding to the emotion information and that is used to adjust the user emotion may be implemented by notifying, by the terminal device, the user of a current emotion state of the user.

The foregoing design allows the user to learn whether the emotion state displayed on the terminal device is accurate.

In a possible design, the notifying, by the terminal device, the user of a current emotion state of the user may be implemented by notifying, by the terminal device, the user of the current emotion state of the user by using a voice or interface display; or sending, by the terminal device, the emotion state to the wearable device, and notifying the user of the current emotion state of the user by using the wearable device.

In the foregoing design, the voice or the interface is used to notify the user emotion state, so that the user can learn whether the emotion state displayed on the terminal device is accurate, and interaction between the user and the terminal device can be implemented to implement human-machine harmony.

In a possible design, the performing, by the terminal device, an operation that is corresponding to the emotion information and that is used to adjust the user emotion may be alternatively implemented by recommending, by the terminal device, activity information or interaction information that is used for adjusting emotion to the user; where the interaction information is used to perform interaction with another user.

Specifically, the server side may determine information of an activity performed by a user around of a good emotion, and sends the activity information to the terminal device, so that the terminal device receives the activity information that is sent by the server and that is to be recommended to the user to adjust the emotion, and displays the activity information to the user. Emotion adjustment methods of people around are usually applicable to another user, and therefore, efficiency of the adjustment is increased by considering the emotion adjustment methods of people around.

In a possible design, after the notifying, by the terminal device, the user of a current emotion state of the user, the method further includes: receiving, by the terminal device, an operation instruction triggered by the user, where the operation instruction is used to instruct the user to recognize the emotion information or modify the emotion information; and then sending, by the terminal device, the emotion information recognized by the user or the modified emotion information to the server.

In the foregoing design, after learning the emotion information, the user may correct displayed incorrect emotion information, so that the server modifies, based on the modified emotion information and data that is used to represent the user physical condition, a weight of each parameter in the user parameter table, thereby improving accuracy of determining the user emotion by the server.

In a possible design, before the terminal device receives the emotion information sent by the server, the method may further include: detecting, by the terminal device, an input instruction triggered by the user, where the input instruction carries activity information corresponding to an activity performed by the user in a second set time period closest to the current time point; sending, by the terminal device, the activity information to the server; receiving, by the terminal device, user information of another user that is sent by the server, where the another user is a user whose activity performed in the second set time period closest to the current time point is the same as the activity of the user, and emotion information of the another user is the same as the emotion information of the user; and displaying, by the terminal device, the user information to the user, so that the user interacts with another user corresponding to the user information.

In the foregoing implementation, the server provides corresponding advice to the user by using a data mining technology and by integrating user emotion information around the user and sensor data of the user. For example, if the user emotion is sad, advice is provided for the user by obtaining data of users whose emotions are happy around the user for integration (for example, if activities in a recent time period of users around the user that are screened by the server side and whose emotions are joyful are running in a park, the user is suggested to run in the park). In the prior art, only adjustment of a personal emotion is considered. However, in reality, emotion adjustment methods of other people, especially emotion adjustment methods of people around are usually helpful to a user. In the foregoing implementation, when the advice is provided, the emotion adjustment methods of the people around are considered by using the data mining technology. This increases efficiency of the adjustment.

In a possible design, the internal of the terminal device may store interaction information corresponding to different emotion information. Therefore, when the terminal device performs the operation that is corresponding to the emotion information and that is used to adjust the user emotion, the terminal device may directly determine the activity information that is corresponding to the emotion information and that is to be recommended to the user, and display the activity information.

In the foregoing design, the terminal device adjusts the user emotion by interacting with the user to humanize the terminal device, which reflects human-machine harmony.

In a possible design, the performing, by the terminal device, an operation that is corresponding to the emotion information and that is used to adjust the user emotion may be implemented by updating, by the terminal device based on the emotion information, a theme, a wallpaper, or a ringtone of the wearable device; or updating, by the terminal device based on the emotion information, a theme, a wallpaper, or a ringtone of the terminal device.

In the foregoing design, one or more manners may be used to adjust the user emotion when the operation that is corresponding to the emotion information and that is used to adjust the user emotion is performed. This delivers higher practical applicability and operability.

According to a second aspect, an embodiment of this application further provides a method for adjusting a user emotion, where the method is applied to a wearable device and includes: detecting, by the wearable device, at least one parameter value that is used to represent a user physical condition; and sending, by the wearable device, the at least one parameter value to the terminal device connected to the wearable device, so that the terminal device performs an emotion adjustment operation for the user based on the at least one parameter value.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

In a possible design, the wearable device receives activity information that is sent by the terminal device and that is to be recommended to the user; and the wearable device displays the activity information. The user carries the wearable device at any moment, and therefore, the real-timeness is higher when the wearable device is used to display the activity information.

In a possible design, the wearable device receives an instruction that is used for updating a theme, updating a wallpaper, updating a ringtone, updating an announcement, or playing the music and that is sent by the terminal device; and the wearable device updates, based on the instruction, the theme, the wallpaper, the announcement, or the ringtone, or plays the music. The user carries the wearable device at any moment, and therefore, the real-timeness and efficiency are higher when the wearable device is used to adjust the ringtone, the theme, the wallpaper, and the like, so as to adjust the user emotion.

According to a third aspect, an embodiment of this application further provides a method for adjusting a user emotion, where the method includes: receiving, by a server, data that is sent by the terminal device and that is used to represent a user physical condition, where the data includes at least one parameter value; obtaining, by the server, a weight corresponding to each of the at least one parameter by searching the user parameter table corresponding to the user, and separately multiplying a parameter value corresponding to each parameter by a weight corresponding to each parameter for summation, so as to obtain an emotion value of the user, where the user parameter table is obtained after data that is used to represent the user physical condition, that is sent by the terminal device, and that is received by the server in a first set time period closest to a time point at which the data is currently received and emotion information that is corresponding to the data and that is confirmed by the user are updated; and generating, by the server, the emotion information based on the emotion value of the user, and sending the emotion information to the terminal device, where the emotion information is used to instruct the terminal device to perform an operation that is corresponding to the emotion information and that is used to adjust the user emotion.

In the foregoing design, the emotion information is determined by the server. This can reduce an occupied computing resource of the terminal device, and improve operation efficiency. In addition, in the prior art, a fixed parameter table is usually used to determine an emotion, and a difference between users is not considered, for example, a user has a relatively high heart rate, but another user has a relatively low heart rate. In this embodiment of this application, an artificial intelligence algorithm is used to update the parameter weight, so as to improve emotion determining accuracy.

In a possible design, after the server sends the emotion value of the user to the terminal device, the method further includes: receiving, by the server, the emotion information that is sent by the terminal device and that is confirmed by the user.

In a possible design, the user parameter table is updated in the following manner: obtaining, by the server, data that is sent by the terminal device in a first set time period and that is used to represent the user physical condition and an emotion value that is confirmed by the user and that is corresponding to the data; and adjusting, based on the determined emotion value and the data corresponding to the determined emotion value, a weight corresponding to a parameter in the data corresponding to the determined emotion value included in the user parameter table corresponding to the user at the current time point, so as to obtain an updated user parameter table.

In the foregoing design, the user parameter table is updated by using the data of the user and the determined emotion, thereby improving accuracy of determining the emotion information.

In a possible design, before the server generates the emotion value of the user based on the user parameter table corresponding to the user and the data that is used to represent the user physical condition, the method further includes: receiving, by the server, activity information that is corresponding to an activity performed by the user in a second set time period closest to the current time point and that is sent by the terminal device; and after the server generates the emotion value of the user based on the user parameter table corresponding to the user and the received data that is used to represent the user physical condition, the method further includes: determining, by the server, a first emotion state corresponding to the emotion value of the terminal user, where different emotion states are corresponding to different emotion value ranges; obtaining, by the server, user information of another user that is in the first emotion state and whose activity information is the same as the activity information of the user; and sending, by the server, the user information of the another user to the terminal device, so that the user interacts with another user corresponding to the user information.

In the foregoing design, the server recommends another user having a same interest with the user to the user, and the two users interact with each other to adjust emotions of the two users at the same time.

According to a fourth aspect, base on a same invention conception as that of the method embodiment, an embodiment of this application further provides an apparatus for adjusting a user emotion. For description of an effect corresponding to the apparatus, refer to the method embodiment. The apparatus is applied to a terminal device and includes: a transceiver, configured to receive first data sent by a wearable device connected to the terminal device, where the first data is at least one parameter value detected by the wearable device for the user; and a processor, configured to: obtain data that is used to represent a user physical condition, where the data includes the first data received by the transceiver; obtain emotion information determined based on the data; and perform an operation that is corresponding to the emotion information and that is used to adjust the user emotion.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

In a possible design, the data that is used to represent the user physical condition further includes second data, and the apparatus further includes: at least one sensor, configured to detect the second data that is used to represent the user physical condition, where the second data includes at least one parameter value. When obtaining emotion information determined based on the data, the processor is specifically configured to obtain emotion information determined based on the first data and the second data.

In a possible design, when obtaining the emotion information determined based on the data, the processor is specifically configured to determine the emotion information based on a parameter value of each parameter in the data and a corresponding weight.

In a possible design, the transceiver is further configured to: send the data obtained by the processor to a server, and receive the emotion information returned by the server based on the data.

In a possible design, when performing the operation that is corresponding to the emotion information and that is used to adjust the user emotion, the processor is specifically configured to notify the user of a current emotion state of the user.

In a possible design, the apparatus may further include: a loudspeaker, configured to provide voice prompt; where the processor is specifically configured to notify the user of the current emotion state of the user by using a voice given by the loudspeaker.

In a possible design, the apparatus may further include: a display device, configured to display prompt information; where the processor is specifically configured to notify the user of the current emotion state of the user by using a display interface of the display device.

In a possible design, the transceiver is further configured to send the emotion state to the wearable device, so that the wearable device notifies the user of the current emotion state of the user.

In a possible design, the processor is further configured to recommend, by using the display device, activity information or interaction information that is used for adjusting emotion to the user; where the interaction information is used to perform interaction with another user.

In a possible design, the first data includes at least one of the following parameter values: a heart rate value, a blood pressure value, and a pulse intensity.

In a possible design, the second data includes at least one of the following parameter values: a voice rate, a voice intensity, a screen pressing intensity, and a facial expression. The at least one sensor includes at least one of the following: a voice receiver, configured to detect the voice rate and/or detect the voice intensity; a pressure sensor, configured to detect the screen pressing intensity; and an image sensor, configured for the facial expression.

In a possible design, the apparatus may further include: a transceiver, configured to: after the processor notifies the user of the current emotion state of the user, receive an operation instruction triggered by the user, and send the emotion information recognized by the user or modified emotion information to the server, where the operation instruction is used to instruct the user to recognize the emotion information or modify the emotion information.

According to a fifth aspect, based on a same invention conception as that of the method embodiment, an embodiment of this application further provides an apparatus for adjusting a user emotion. For description of an effect corresponding to the apparatus, refer to the method embodiment. The apparatus is applied to a wearable device and includes: at least one sensor, configured to detect at least one parameter value that is used to represent a user physical condition; and a transceiver, configured to send the at least one parameter value to the terminal device, so that the terminal device performs an emotion adjustment operation for the user based on the at least one parameter value.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

In a possible design, the transceiver is further configured to receive activity information that is sent by the terminal device and that is to be recommended to the user; and a display device is configured to display the activity information.

In a possible design, the transceiver is further configured to receive an instruction that is used for updating a theme, updating a wallpaper, updating an announcement, updating a ringtone, or playing music and that is sent by the terminal device; the display device is further configured to display the wallpaper or the theme; the apparatus further includes a processor, configured to: update, based on the instruction, the theme, the wallpaper, the announcement, or the ringtone, or play the music; the display device is further configured to display the wallpaper or the theme that is updated by the processor; and the apparatus further includes a loudspeaker, configured to: give the announcement updated by the processor, or give the ringtone updated by the processor, or play the music.

According to a sixth aspect, an embodiment of this application further provides an apparatus for adjusting a user emotion, where the apparatus is applied to a terminal device and includes: a data collection module, configured to obtain data that is used to represent a user physical condition, where the data includes first data, and the first data is at least one parameter value detected for the user by a wearable device connected to the terminal device; a data exchange module, configured to obtain emotion information determined based on the data; and an execution module, configured to perform an operation that is corresponding to the emotion information and that is used to adjust the user emotion.

In a possible design, the data that is obtained by the data collection module and that is used to represent the user physical condition further includes second data, and the second data is at least one parameter value of the user detected by the terminal device; and the data exchange module is specifically configured to obtain emotion information determined based on the first data and the second data.

In a possible design, the data exchange module is specifically configured to: determine the emotion information based on a parameter value of each parameter in the data and a corresponding weight.

In a possible design, the data exchange module is further configured to: send the obtained data to a server, and receive the emotion information returned by the server based on the data.

In a possible design, the execution module is specifically configured to: notify the user of a current emotion state of the user.

In a possible design, the execution module is specifically configured to: notify the user of the current emotion state of the user by using a voice or interface display; or send the emotion state to the wearable device, and notify the user of the current emotion state of the user by using the wearable device.

In a possible design, the execution module is specifically configured to: recommend activity information or interaction information that is used for adjusting emotion to the user; where the interaction information is used to perform interaction with another user.

In a possible design, the first data includes at least one of the following parameter values: a heart rate value, a blood pressure value, and a pulse intensity.

In a possible design, the second data includes at least one of the following parameter values: a voice rate, a voice intensity, a screen pressing intensity, and a facial expression.

In a possible design, the data exchange module is further configured to: after the execution module notifies the user of the current emotion state of the user, receive an operation instruction triggered by the user, and send the emotion information recognized by the user or modified emotion information to the server, where the operation instruction is used to instruct the user to recognize the emotion information or modify the emotion information.

According to a seventh aspect, an embodiment of this application further provides an apparatus for adjusting a user emotion, including: a detection module, configured to detect at least one parameter value that is used to represent a user physical condition; and a sending module, configured to send the at least one parameter value to a terminal device connected to the wearable device, so that the terminal device performs an emotion adjustment operation for the user based on the at least one parameter value.

In a possible design, the apparatus further includes: a receiving module, configured to receive activity information that is sent by the terminal device and that is to be recommended to the user; and a display module, configured to display the activity information.

In a possible design, the apparatus further includes: a receiving module, configured to receive an instruction that is used for updating a theme, updating a wallpaper, updating an announcement, updating a ringtone, or playing the music and that is sent by the terminal device; and a processing module, configured to: update, based on the instruction, the theme, the wallpaper, the announcement, or the ringtone, or play the music.

DETAILED DESCRIPTION OF ILLUSTRATIVE EMBODIMENTS

To make the objectives, technical solutions, and advantages of this application clearer, the following further describes this application in detail with reference to the accompanying drawings.

Currently, there may be some dedicated training systems. For example, in an existing heart rate variability (HRV) system, some dedicated collection apparatuses are used to collect heart rates, oxyhemoglobin saturation, pulse intensities, and the like, and provide some adjustment solutions based on the collected data, for example, relaxation training, music accommodation, and autonomic regulation are used to help a user adjust an emotion.

The foregoing solution or other solutions similar to the foregoing solution may help, to some extent, a user adjust an emotion. However, the foregoing solution has a lot of room for improvement. Specifically, the foregoing emotion adjustment method needs to be implemented by using a dedicated collection apparatus, and does not consider a difference between different users, and a provided emotion adjustment solution may not change intelligently in real time. Therefore, the emotion adjustment manner may not be intelligent and may not have an obvious effect for many users.

Based on this, embodiments of this application provide a method and an apparatus for adjusting a user emotion, so as to adjust people's emotions in a convenient and effective way. The method and the apparatus are based on a same invention conception. Because a problem-solving principle of the apparatus is similar to that of the method, mutual reference may be made to implementations of the method and the apparatus, and repeated description is not provided.

Figure 1:
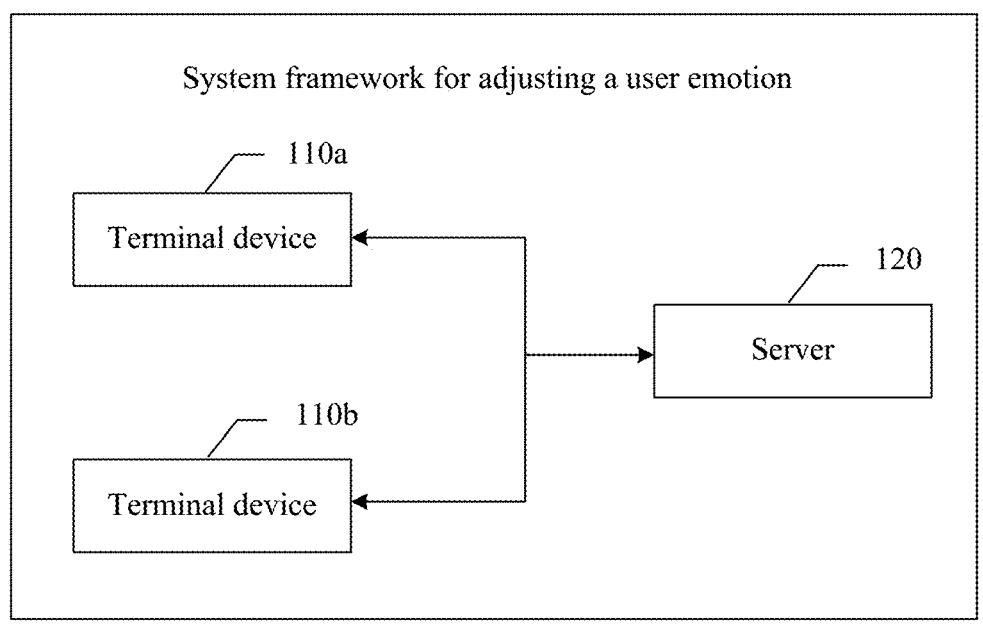
FIG. 1 is a schematic diagram of a system framework for adjusting a user emotion according to an embodiment of this application.

A system framework for adjusting a user emotion that is applied to this embodiment of this application includes at least one terminal device and server. As shown in FIG. 1, the system framework for adjusting a user emotion shown in FIG. 1 includes a terminal device 110a, a terminal device 110b, and a server 120.

The terminal device 110a and the terminal device 110b are connected to each other in a wireless manner, and available wireless manners include but are not limited to various wireless short range communications manners such as Bluetooth, Near Field Communication (NFC for short), ZigBee, infrared, and Wireless Fidelity (Wi-Fi for short). This is not specifically limited in this embodiment of this application. It may be understood that the terminal device 110a may communicate with the terminal device 110b in a mobile communications manner. The terminal device 110a and the terminal device 110b may be connected to the server 120 by using a wireless communications technology. An available wireless communications manner may be mobile communications, and includes but is not limited to the second generation mobile telecommunications, the third generation mobile telecommunications, the fourth generation mobile telecommunications, or the fifth generation mobile telecommunications, or may be another wireless communications manner such as Wi-Fi or another wireless short range communications manner. This is not specifically limited in this embodiment of this application.

The server of this embodiment of this application may be a service computer, a mainframe computer, or the like. The terminal device of this embodiment of this application includes but is not limited to a personal computer, a hand-held or laptop device, a mobile device (such as a mobile phone, a tablet computer, a smart band, a smartwatch, or a personal digital assistant). The following uses an intelligent mobile terminal as an example to describe in detail the solution provided in this embodiment of this application.

Figure 2A:
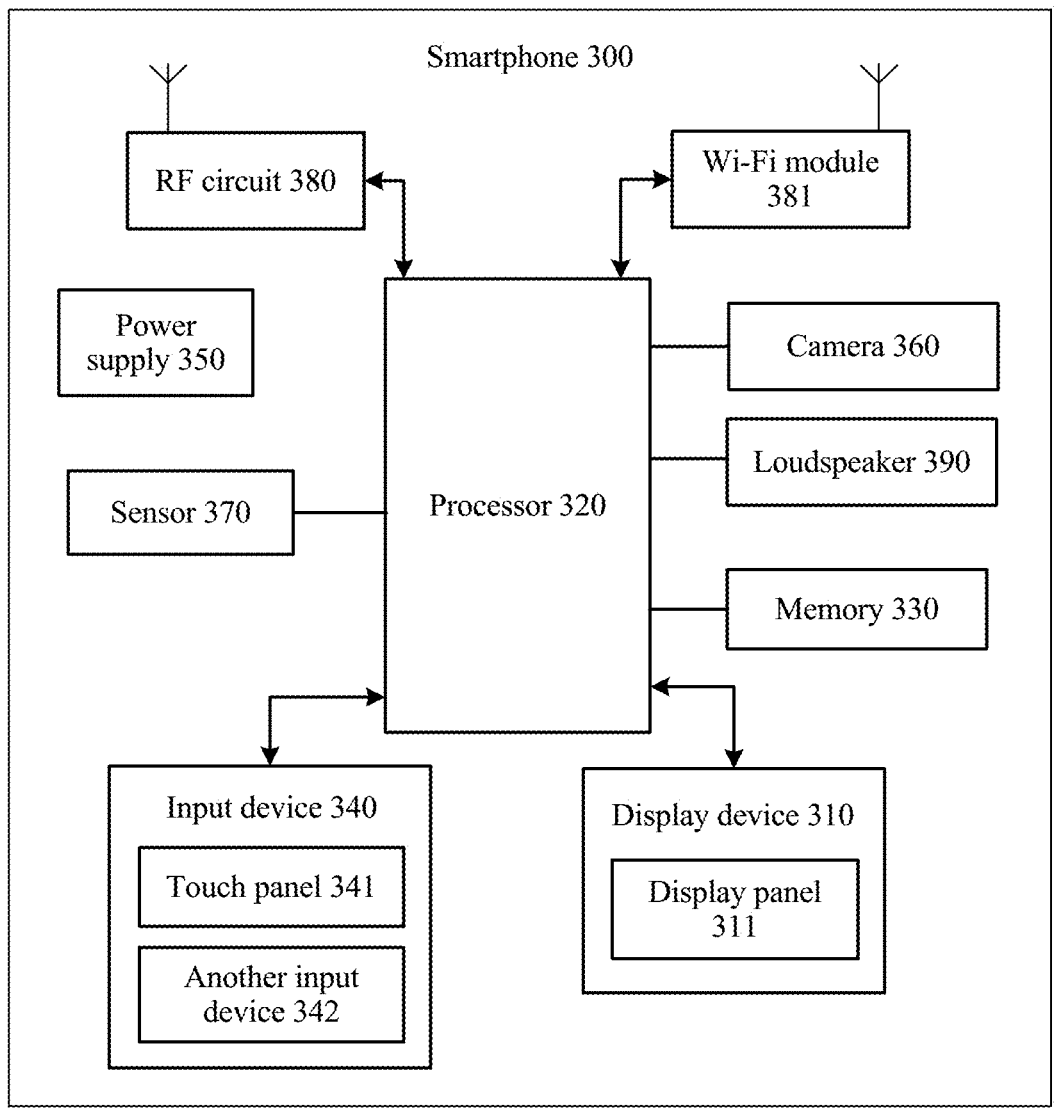
FIG. 2A is a schematic diagram of a terminal device according to an embodiment of this application.

The following uses interaction between a terminal device and a server as an example to describe in detail the method for adjusting a user emotion. For example, the terminal device is a smartphone 300, as shown in FIG. 2A. The smartphone 300 includes a display device 310, a processor 320, and a memory 330. The memory 330 may be configured to store a software program and data, and the processor 320 runs the software program and the data that are stored in the memory 330, so as to execute various function applications of the smartphone 300 and perform data processing. The memory 330 may mainly include a storage program area and a storage data area, where the storage program area may store an operating system, an application program required by at least one function, and the like, and the storage data area may store data (such as audio data and a phone book) that is created based on use of the smartphone 300 and the like. In addition, the memory 330 may include a high-speed random access memory, and may include a non-volatile memory, such as at least one magnetic disk storage device, a flash storage device, or another volatile solid-state storage device. As a control center of the smartphone 300, the processor 320 connects various parts of the entire terminal by using various interfaces and lines, and performs, by running or executing a software program and/or data that are/is stored in the memory 330, various functions of the smartphone 300 and data processing, so as to perform overall monitoring on the terminal. The processor 320 may include one or more general purpose processors, and may further include one or more digital signal processors (DSP for short), which are configured to perform corresponding operations, so as to implement the technical solutions provided in this embodiment of this application.

The smartphone 300 may further include an input device 340, which is configured to: receive digit or character information that is input or a contact touch operation/non-contact gesture, and generate signal input related to user configuration and function control of the smartphone 300, and the like. Specifically, in this embodiment of this application, the input device 340 may include a touch panel 341. The touch panel 341, also referred to as a touchscreen, can collect a touch operation (for example, an operation performed by the user on or near the touch panel 341 by using any appropriate object or accessory such as a finger or a stylus) of the user on or near the touch panel 341, and drive a corresponding connection apparatus based on a preset program. Optionally, the touch panel 341 may include two parts: a touch detection apparatus and a touch controller. The touch detection apparatus detects a touch direction of the user, detects a signal brought by the touch operation, and transmits the signal to the touch controller. The touch controller receives touch information from the touch detection apparatus, converts the touch information to touch point coordinates, and sends the touch point coordinates to the processor 320, and can receive and perform a command sent by the processor 320. For example, when the user taps, with a finger, an image thumbnail on the touch panel 341, the touch detection apparatus detects a signal brought by the tap, and then transmits the signal to the touch controller. The touch controller converts the signal to coordinates, and then sends the coordinates to the processor 320. The processor 320 determines, based on the coordinates and a type of the signal (tap or double tap), an operation performed on the image (such as image enlargement or an image displaying in full screen), and then determines that a memory space needs to occupy to perform the operation. If the memory space needs to occupy is less than a free memory, the enlarged image is displayed, in full screen, on a display panel 311 included in the display device to implement image display.

The touch panel 341 may be implemented by using a plurality of types, such as a resistive type, a capacitive type, an infrared ray, and a surface acoustic wave. In addition to the touch panel 341, the input device 340 may include another input device 342, where the another input device 342 may include but is not limited to one or more of a physical keyboard, a function key (for example, a volume control key or an on/off key), a trackball, a mouse, and a joystick.

The display panel 311 included in the display device 310 is configured to display information that is input by the user, information provided for the user, various menu interfaces of the terminal device 300, and the like, and is mainly configured to display images in the smartphone 300 in this embodiment of this application. Optionally, the display panel 311 may be configured in the form of a liquid crystal display (LCD for short), an organic light-emitting diode (OLED for short), or the like. In some other embodiments, the touch panel 341 may cover the display panel 311 to form a touch display screen.

In addition, the smartphone 300 may include a power supply 350 that is configured to supply power to other modules and a camera 360 that is configured to take a picture or record a video. The smartphone 300 may further include one or more sensors 370, for example, a light sensor, a voice receiver, a pressure sensor, and an image sensor. The light sensor is configured to collect light values. The voice receiver is configured to collect voice volumes, voice frequency values, voice rates, voice intensities, and the like. The pressure sensor is configured to collect screen touch intensity values of a user. The image sensor is configured to take a picture, and the like.

The smartphone 300 may further include a transceiver. The transceiver includes a wireless communications module, for example, a radio frequency (RF for short) circuit 380, configured to perform network communication with a wireless network device; may further include a Wi-Fi module 381, configured to perform Wi-Fi communication with another device; and may further include an infrared module, a Bluetooth module, or the like. The smartphone 300 may further include a loudspeaker 390. The loudspeaker 390 is configured to play music, provide voice prompt, play an announcement, or the like.

Figure 2B:
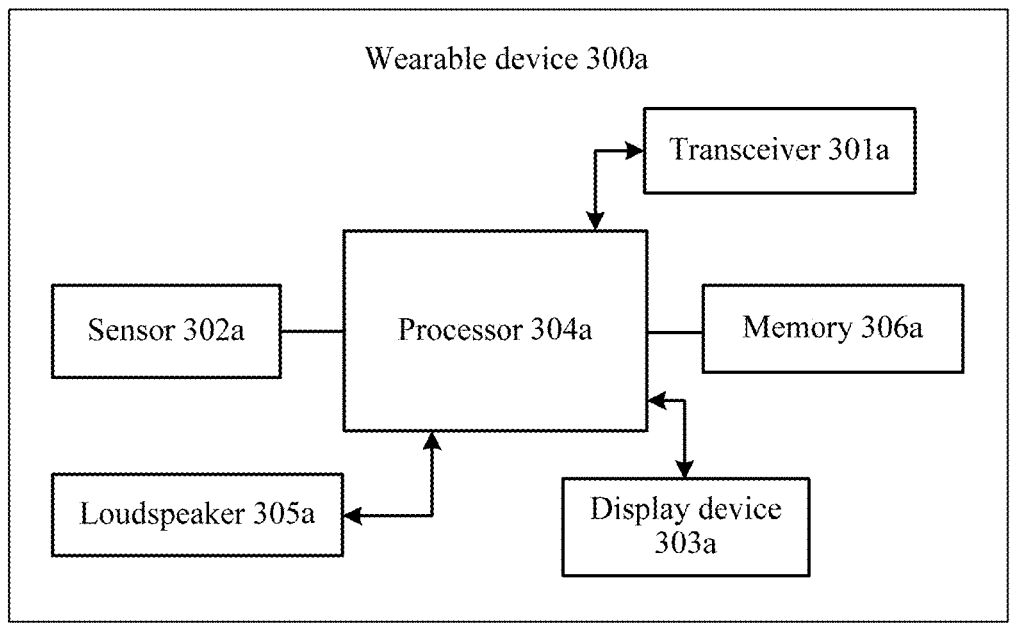
FIG. 2B is a schematic diagram of a wearable device according to an embodiment of this application.

In this embodiment of this application, in addition to the foregoing smartphone 300, the system for adjusting a user emotion further includes a wearable device 300a such as a band or a watch. As shown in FIG. 2B, the wearable device 300a may include a transceiver 301a. The transceiver 301a may include at least one of the following: an infrared module, a Bluetooth module, a Wi-Fi module, and the like. That is, the wearable device communicates with the smartphone 300 by using the transceiver 301a. In addition, the wearable device 300a may include a radio frequency circuit, and specifically, is connected to the server by using the radio frequency circuit. The wearable device may include one or more sensors 302a such as a temperature sensor, a pulse sensor, and a blood pressure sensor. The temperature sensor is configured to collect user temperatures. The pulse sensor is configured to collect user pulses. The blood pressure sensor is configured to collect user blood pressures. The wearable device may further include a display device 303a. The display device 303a is configured to display prompt information, a picture, a theme, a wallpaper, activity information, or the like. The wearable device 300a may further include a processor 304a, configured to perform an operation such as data receiving of various sensors. The wearable device 300a may further include a loudspeaker 305a. The loudspeaker 305a is configured to provide voice prompt, play music, play a ringtone, and the like. The wearable device 300a further includes a memory 306a. The memory 306a may be configured to store data, a software program performed by the processor 304a, and the like.

Before the user emotion adjustment method of the terminal is described in detail, terms used in the embodiments of this application are explained first.

1. Data that is used to represent a user physical condition may be data that directly or indirectly represents the user physical condition. The data includes at least one parameter value of the user, such as a heart rate, a temperature, a pulse, a blood pressure, an intensity of a light felt by the user, a display device touch intensity of the user, a voice volume, a voice frequency, a voice intensity, a voice rate, or a facial expression.

2. Emotion information is used to reflect a current emotion and a health status of the user. The emotion may be divided into a normal emotion and an abnormal emotion. For example, joyful and happy are normal emotions, and angry, sad, and scared are abnormal emotions. The health status is divided into healthy, unhealthy, and the like. The abnormal emotion also belongs to the unhealthy state. Certainly, the unhealthy state further includes a state in which the user may get sick, such as conditions of hyperpyrexia or fever, heartbeat pause, or the like. The emotion information may include a user emotion value and/or an emotion state of the user. The emotion state may include the normal emotion or the abnormal emotion, and may further include joyful, sad, happy, angry, excited, and the like.

Different emotion states are corresponding to different emotion value ranges. For example, people have a relatively high emotion fluctuation in an exited emotion, and therefore, an emotion value range corresponding to excitement is relatively large. An emotion fluctuation is relatively low for the joy, and therefore, an emotion value range corresponding to the joy is relatively small. A specific emotion value range may be set based on a percentage of data of each condition and a practical situation. This is not specifically limited in this embodiment of this application.

In addition, different emotion states may be corresponding to different parameter value ranges. For example, when a blood pressure is greater than a first preset value, a pulse is within a preset range, and a temperature is less than a second preset value, it indicates a scare emotion.

3. Activity information is used to describe an activity that the user participates in a period of time such as walking in a park, running, or reading; or may be some advice for the user, such as reminding the user of keeping a good emotion and not being excited, or reminding the user of using sun cream.

4. Interaction information is used to represent interaction between the user and another user.

5. A user parameter table includes weights corresponding to different parameters. For example, a weight corresponding to the temperature is a1, and a weight corresponding to the pulse is a2.

6. An operation for adjusting a user emotion includes but is not limited to displaying the activity information, displaying the interaction information, playing music, popping a picture, or playing a voice, modifying a theme, modifying a wallpaper, and interaction with another user, or modifying an announcement, providing vibration prompt, and notifying the user of an emotion state of the user. The operation may further include updating a theme, a wallpaper, an announcement of the wearable device, popping a picture and playing a voice on the wearable device, and the like.

Figure 3:
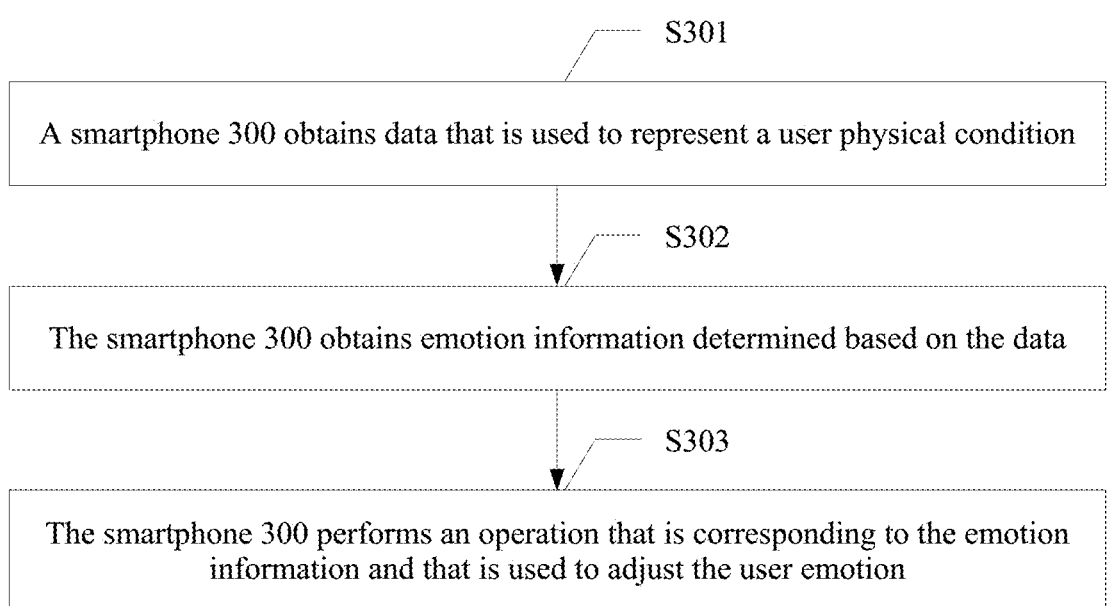
FIG. 3 is a flowchart of a method for adjusting a user emotion according to an embodiment of this application.

FIG. 3 is a schematic diagram of a method for adjusting a user emotion.

When a user wears a band or a watch, the band or the watch monitors a heart rate value, a blood pressure value, a temperature, a pulse intensity, and the like of the user, and sends the heart rate value, the blood pressure value, the temperature, the pulse intensity, and the like of the user to a smartphone 300 by using Bluetooth or infrared.

S301. The smartphone 300 obtains data that is used to represent a user physical condition.

The data includes first data, where the first data is at least one parameter value detected for the user by a wearable device connected to the terminal device. The first data includes a heart rate value, a blood pressure value, a temperature, a pulse intensity, and the like.

Optionally, the wearable device may be a band or a watch. The band or the watch may periodically, for example, every hour, report the data that is used to represent the user physical condition. For example, the band or the watch collects data at a plurality of time points of a period, then calculates an average value of parameter values that are corresponding to a same parameter of the user and that are collected at the plurality of time points, and sends the average value to the smartphone 300. Certainly, the band or the watch may not perform a statistical operation after collecting data of the user at a plurality of time points of a period, and directly send the data to the smartphone 300.

S302. The smartphone 300 obtains emotion information determined based on the data.

S303. The smartphone 300 performs an operation that is corresponding to the emotion information and that is used to adjust the user emotion.

A quantity of parameters included in the data that is used to represent the user physical condition is not specifically limited in this embodiment of this application.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

In step S302, when the smartphone 300 obtains the emotion information determined based on the data that is used to represent the user physical condition, the smartphone 300 may determine the emotion information based on the data.

In addition, the smartphone 300 may detect second data to improve a user emotion determining accuracy. Therefore, the data that is obtained by the smartphone 300 and that is used to represent the user physical condition may further include the second data, where the second data includes at least one parameter value of the user. The second data may include at least one of the following parameter values: a voice rate, a voice intensity, a screen pressing intensity, a facial expression, and the like.

In a possible implementation, when the smartphone 300 obtains the emotion information determined based on the data, the smartphone 300 may determine the emotion information based on a threshold corresponding to each parameter and a relationship between the parameter and the threshold. For example, the data includes only a parameter, a temperature, and generally, a normal range of the temperature is 36-37° C. The smartphone 300 may collect statistics on temperature values in a period T, for example, an hour. The smartphone 300 may collect statistics on an average value of user temperatures in an hour. If the average value of the user temperatures is not within the normal range, it is determined that the user is having a fever. The smartphone 300 displays interaction information to the user, for example, displaying "Your current temperature is not within the normal range, please pay attention".

For another example, the data includes three parameters: a temperature, a pulse, and a blood pressure, where a normal range of the blood pressure is 90-130 mmhg, and a normal range of the pulse is 60-100 times per minute. It is assumed that the blood pressure of the user is greater than the normal range, for example, the blood pressure is greater than 130, a pulse is normal, for example, the pulse is within a range of 60-100, and a temperature is relatively low, for example, the temperature is less than 36.2. This case may occur when the user is extremely scared or frightened. When determining that the user is in this state, the smartphone 300 may play music to alleviate the user emotion, and may further change a displayed wallpaper to, for example, a picture of the ocean. In this embodiment of this application, a music library, a picture library, and the like may be configured based on different emotions. A case in which the blood pressure of the user is relatively high, a pulse of the user is relatively fast, and a temperature of the user is relatively high may occur when the user is extremely excited. When determining that the user is in this state, the smartphone 300 may play music to alleviate the user emotion, for example, light music with a relatively slow rhythm.

It should be noted that, in this embodiment of this application, a threshold may be set for a state corresponding to each parameter. For example, when the blood pressure of the user is greater than a first threshold, it indicates that the blood pressure of the user is relatively high. Threshold may be set for other parameters, which are not listed one by one in this embodiment of this application.

In another possible implementation, the smartphone 300 may determine the emotion information based on a parameter value of each parameter in the data and a corresponding weight. Specifically, the smartphone 300 may maintain a user parameter table, and the user parameter table includes weights corresponding to different parameters. When determining the emotion information based on a plurality of parameter values, the terminal device may obtain a weight corresponding to each of the at least one parameter by searching the user parameter table, separately multiply a parameter value corresponding to each parameter by a weight corresponding to each parameter, and the perform summation, so as to obtain an emotion value of the user.

The user parameter table includes weights corresponding to different parameters. For example, a weight of a voice volume is a1, a heart rate value is a2, and a voice frequency value is a3. Weights corresponding to other parameters are not listed one by one in this embodiment of this application.

Specifically, a current emotion value of the user is calculated based on stored weights, for example, an emotion value E=a1*voice volume+a2*heart rate value+a3*voice frequency value+ . . . .

Figure 4:
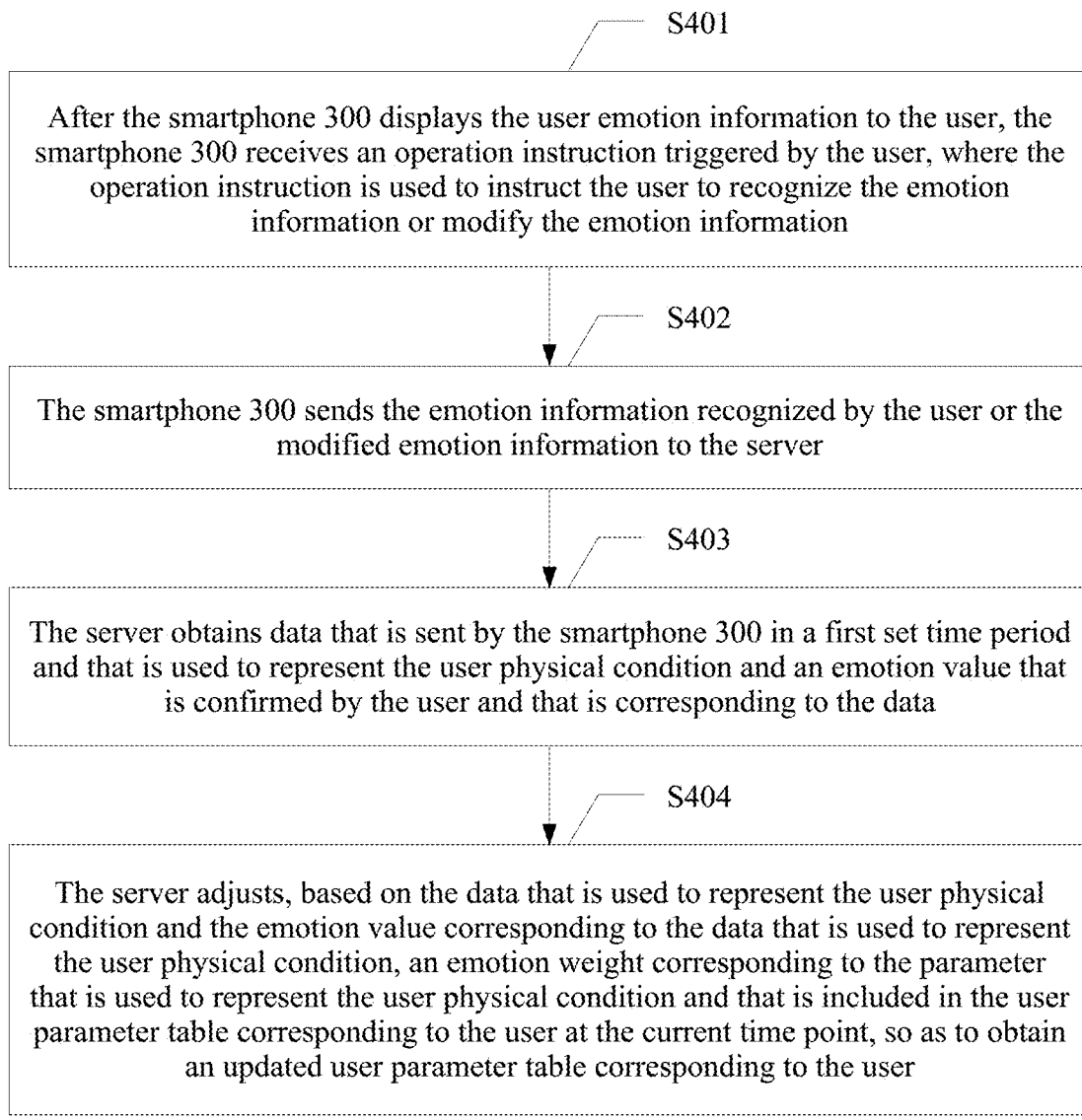
FIG. 4 is a schematic diagram of a flowchart of a method for updating a user parameter table according to an embodiment of this application.

In this embodiment of this application, the user parameter table may be configured on the smartphone 300. The user parameter may be alternatively sent by a server to the smartphone 300. The server may periodically update the user parameter table, and then send the updated user parameter table to the smartphone 300. If the emotion information can directly represent the emotion state, the smartphone 300 may display determined user emotion information to the user; or if the emotion information cannot directly represent the emotion state, the smartphone 300 determines the emotion state of the user based on the emotion information, and then displays the emotion state of the user to the user, so as to remind the user of confirming whether the emotion state is accurate. When notifying the user of the current emotion state of the user, the smartphone 300 may notify the user of the current emotion state of the user by using a voice or a display interface; or the smartphone 300 may send the emotion state to the wearable device, and notify the user of the current emotion state of the user by using the wearable device. Specifically, the emotion state may be displayed to the user periodically for confirmation. Specifically, a procedure of updating the user parameter table is shown in FIG. 4.

S401. After the smartphone 300 displays the user emotion information to the user, the smartphone 300 receives an operation instruction triggered by the user, where the operation instruction is used to instruct the user to recognize the emotion information or modify the emotion information.

Certainly, the user may configure the smartphone 300 based on a condition of the user without triggering the display operation instruction.

S402. The smartphone 300 sends the emotion information recognized by the user or the modified emotion information to the server, so that the server receives the emotion information that is sent by the smartphone 300 and that is confirmed by the user.

Figure 5A:
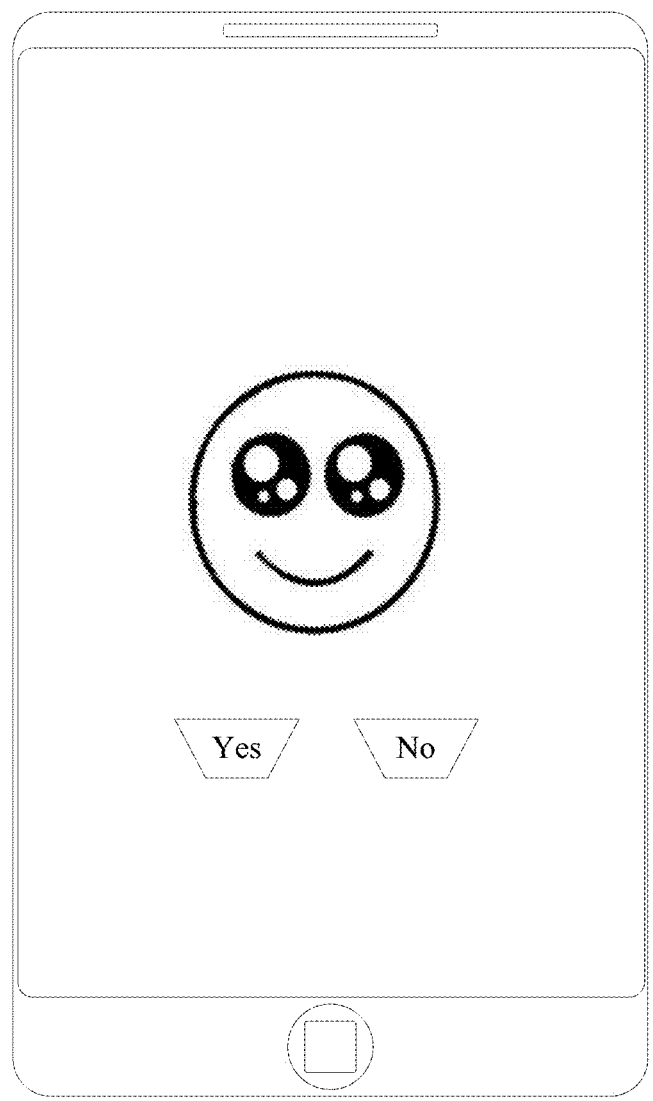
FIG. 5A to FIG. 5C are schematic diagrams for displaying a user emotion state according to an embodiment of this application.
Figure 5B:
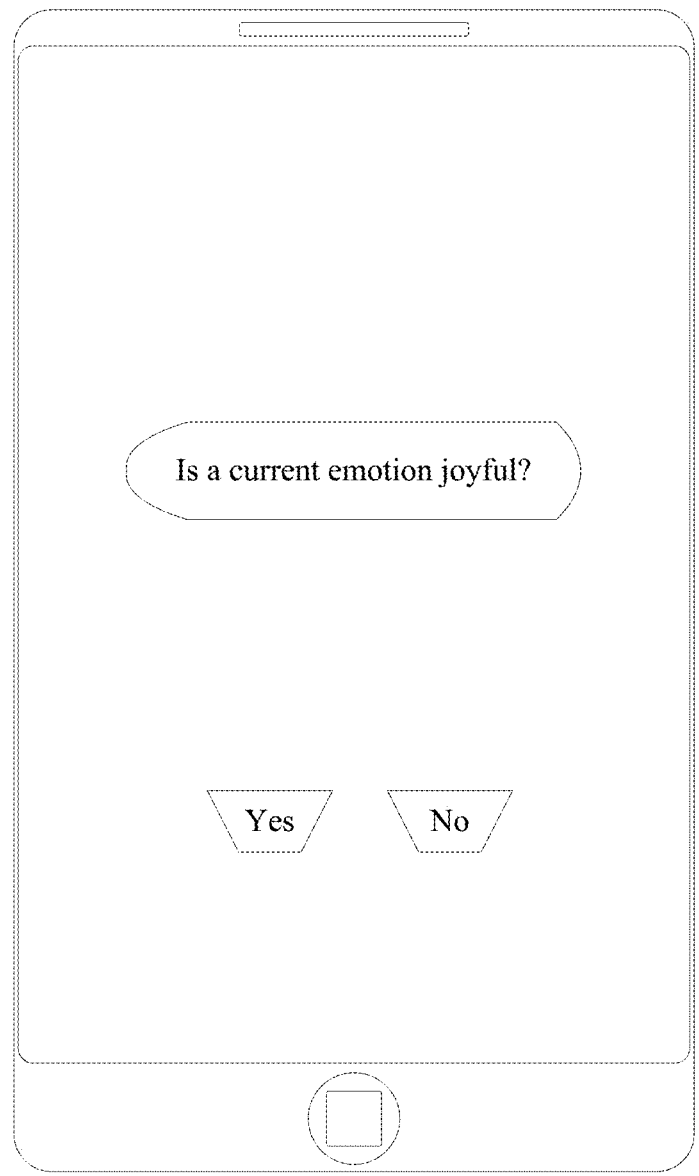
Figure 6:
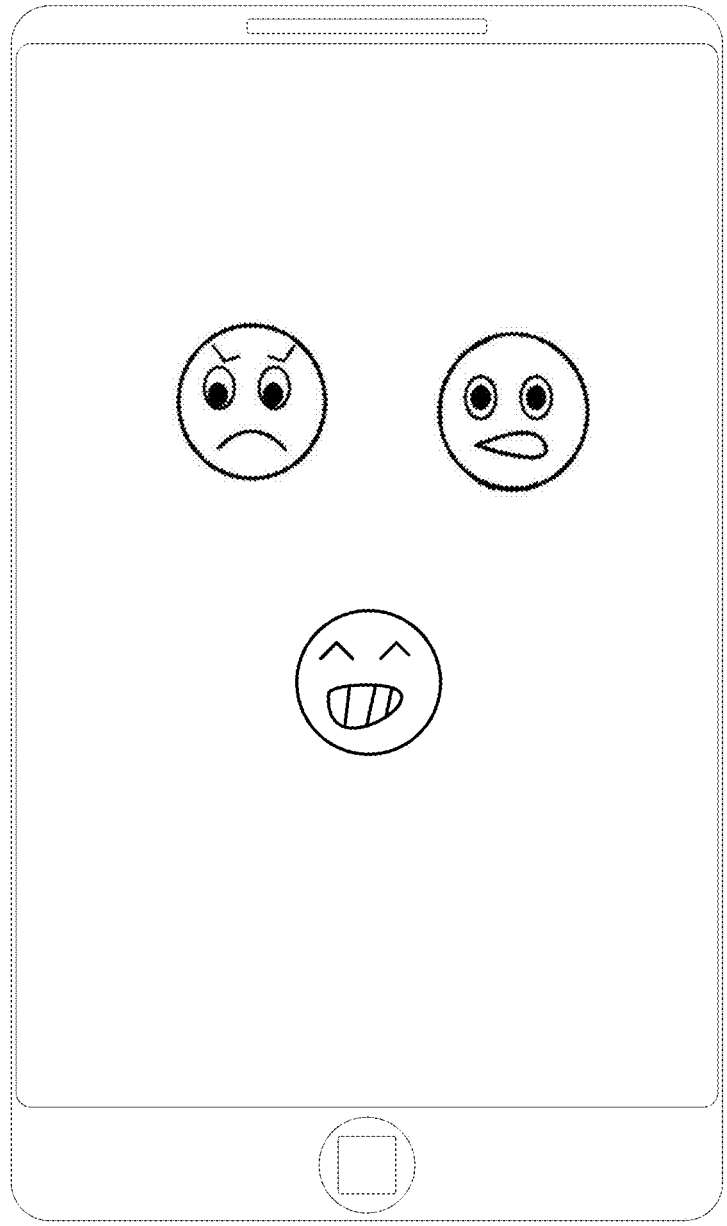
FIG. 6 is a schematic diagram of an interface for displaying a user emotion state selection according to an embodiment of this application.

For example, if a current emotion of the user is joyful, the current emotion information is joy. The emotion information may be displayed to the user in various forms, for example, the emotion information is displayed on a display interface shown in FIG. 5A or FIG. 5B. The display interface further displays icons that the user may use for confirmation, for example, "yes" and "no" shown in FIG. 5A or FIG. 5B. For example, in FIG. 5A, when the user taps the icon "no", a display interface corresponding to FIG. 6 may be displayed, so that the user may select a corresponding emotion icon.

Figure 5C:
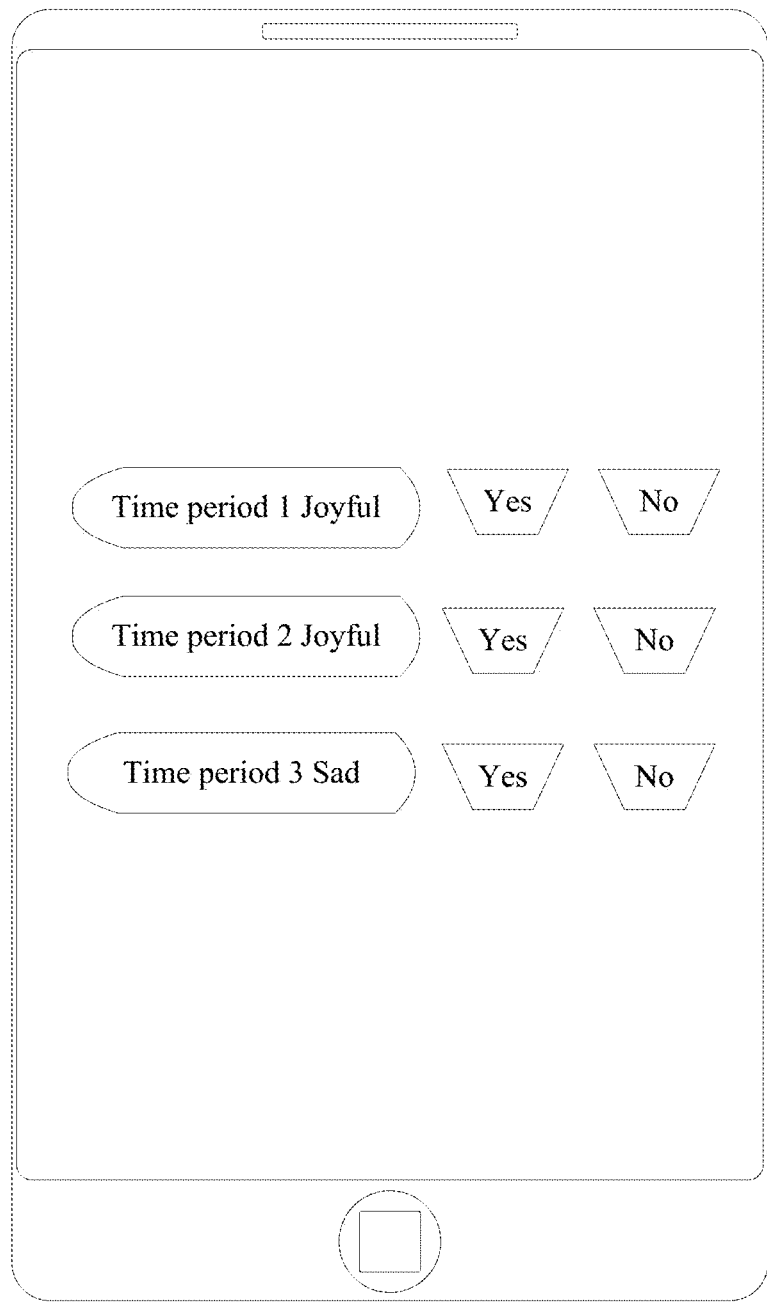

In addition, when the smartphone 300 displays the emotion information to the user, emotion information calculated by a server 120 based on uploaded data that is used to represent the user physical condition may be displayed to the user by time period, and a form is shown in Table 1. A specific display form may be shown in FIG. 5C.

TABLE 1

| | |
|---|---|
| Time period 1 | Joy |
| Time period 2 | Joy |
| Time period 3 | Sadness |

After the user modifies the emotion information based on an actual situation of the user, the smartphone 100 may upload the modified emotion information to the server, so that the server updates the stored user parameter table based on the emotion information confirmed by the user.

The server may collect data of different users, including uploaded data and emotion information of each user that is used to represent the user physical condition. The data is stored in a database based on a user ID, and a form of single user data is shown in Table 2.

TABLE 2

| Time period 1 | Data 1 | Emotion information 1 (joy) | Whether it is confirmed by the user (yes) |
| --- | --- | --- | --- |
| Time period 2 | Data 2 | Emotion information 2 (joy) | Whether it is confirmed by the user (no) |
| Time period 3 | Data 3 | Emotion information 3 (sadness) | Whether it is confirmed by the user (yes) |

For example, the data 1 may include a force of tapping a keyboard, a pressure value sensed by a screen pressure sensor, a heart rate value, and a pulse intensity. Parameters included in the data 2 may be the same or different from those included in the data 1. For example, on the basis of all parameters included in the data 1, the data 2 may further include a volume and a voice frequency, and expression data. For example, in a period of collecting the data 1, the user does not perform communication, but the user performs voice communication with another user in a period of collecting the data 2. A camera is started in the voice communication process to obtain expression data of the user. Certainly, parameters included in the data 3 may be the same as or different from those included in the data 1 and the data 2. This is not specifically limited in this embodiment of this application.

It should be noted that if a confirmation field of the user is "yes", it indicates that emotion information determining is correct, or if the confirmation field of the user is "no", it indicates that the user has not performed confirmation or updating. In storage, another time period is used when the user emotion information changes, or if the emotion information remains, only the time period and the data used to represent the user physical condition are updated. That is, if emotion information that is of a time period closest to a current time point and that is searched by the server in the database is the same as the user emotion information currently confirmed, data that is used to represent the user physical condition and that is of the time period closest to the current time point and the time period are updated.

Optionally, the server updates the user parameter table corresponding to the user in the following manner.

S403. The server obtains data that is sent by the smartphone 300 in a first set time period and that is used to represent the user physical condition and an emotion value that is confirmed by the user and that is corresponding to the data.

S404. The server adjusts, based on the data that is used to represent the user physical condition and the emotion value corresponding to the data that is used to represent the user physical condition, a weight corresponding to the parameter that is used to represent the user physical condition and that is included in the user parameter table corresponding to the user at the current time point, so as to obtain an updated user parameter table corresponding to the user, where the first set time period may be a week, two weeks, a day, or the like. That is, the server updates the user parameter table at the first set time period.

Optionally, after obtaining the data that is sent by the smartphone 300 and that is used to represent the user physical condition and the emotion value conformed by the user, the server may first perform cleansing and de-duplication processing on the data used to represent the user physical condition and the emotion value. The server may periodically perform cleansing or the de-duplication processing on the data used to represent the user physical condition and the emotion value, for example, a week, two weeks, or a day. This is not specifically limited in this embodiment of this application.

Specifically, when adjusting, based on the data that is used to represent the user physical condition and the emotion value corresponding to the data that is used to represent the user physical condition, weights corresponding to different parameters included in the user parameter table corresponding to the user of the smartphone 300 at the current time point, the server may train and adjust the weights by using an artificial intelligence algorithm.

The artificial intelligence algorithm may include but is not limited to a neural network, a genetic algorithm, and a polynomial algorithm.

For example, the updated user parameter table may be shown in Table 3.

TABLE 3

| User ID 1 | Parameter 1 |
| --- | --- |
| User ID 2 | Parameter 2 |

The parameter 1 in Table 3 may include weights corresponding to a voice volume, a voice frequency, a force of tapping a keyboard, a pressure value sensed by a screen pressure sensor, a heart rate value, a pulse intensity, a facial expression, and the like of the user ID 1. The parameter 2 includes a weight of each parameter of the user ID 2.

In the prior art, a fixed parameter table is used for determining an emotion without considering a difference between users, for example, a user has a relatively high heart rate, but another user has a relatively low heart rate. Updating the parameter by using the artificial intelligence algorithm may improve emotion determining accuracy.

In a possible implementation, the smartphone 300 may further detect the parameter value of the user by using a built-in sensor of the smartphone 300, so that the smartphone 300 determines emotion information based on the received parameter value that is sent by the band or the watch and the detected parameter value.

For example, the parameter value of the user may be detected by using a built-in voice receiver of the smartphone 300. When the user is in a relatively dangerous condition such as rock climbing, working at heights, or driving, the smartphone 300 can obtain a voice-related parameter value of the user by self-starting or manual starting. For example, the smartphone determines, by detecting an altitude or a moving speed, whether to start to obtain the voice-related parameter value. The related parameter value may include a voice volume, a voice rate, a voice intensity, and the like. This is not specifically limited herein. That the user is driving is used as an example. When the user is in a driving state, a driving emotion may be affected by other drivers around or a road condition. For example, when a traffic jam occurs, the user may be relatively anxious, or even relatively emotional and speak irritably. When the user is emotional, the user may speak fast or with a high volume. Therefore, the smartphone 300 may determine the user emotion based on this. When the user is emotional, the smartphone 300 may remind the user of "please do not be so emotional". The smartphone 300 may further select, from music stored in the database, soothing or pleasing music to improve the user emotion. If the user is currently relatively sad, the smartphone 300 may play positive and brisk music to improve the user emotion. In this embodiment of this application, in addition to playing the music, the user emotion may be alternatively improved by popping a picture, playing a voice, or the like. For example, when the user is in a sad emotion, a voice joke is played, a grimace is displayed, or the like to improve the user emotion.

In addition, when the user performs voice communication, the terminal may detect information of the user such as a voice frequency, a voice rate, a voice intensity, or a voice volume. The user emotion is determined with reference to detected voice-related data and other detected data related to the user physical condition. For example, it may be determined, with reference to the detected voice-related data, the detected user heart rate, pulse, or the like, whether there is a high fluctuation in the user emotion or what a specific emotion state the user is in. Similarly, when a user performs video communication, facial expression data of the user may be obtained by using a built-in image sensor of the smartphone 300. The expression is used to determine a specific emotion state of the user. The user emotion is determined by using parameters obtained through voice detection and the facial expression data, and therefore ensuring higher accuracy.

The facial expression detection occupies a relatively large quantity of resources. Therefore, in this embodiment of this application, a trigger condition may be set for starting the facial expression detection. For example, the facial expression detection is started when it is detected that a user heart rate is relatively high or a pulse is in an abnormal range. It may be understood that a similar trigger condition may be set to start the voice detection.

Certainly, in this embodiment of this application, it is not limited to use one, two, or a plurality of sensors to obtain the data of the user that is used to represent the user physical condition. For example, the user emotion may be determined by using parameter values obtained by the image sensor, the voice receiver, and the pressure sensor.

Compared with an abnormal emotion, when the user inputs, in a normal emotion, information by using an input panel, an input frequency collected by the pressure sensor is low, and a pressure value is relatively small; a volume collected by using the voice receiver is low, and expression information collected by using the image sensor is normal. Therefore, the user emotion is determined by using the pressure sensor, the voice receiver, and the image sensor.

In this embodiment of this application, when the operation that is used to adjust the user emotion is performed, the corresponding operation may be performed based on current states of the terminal device and the wearable device or a current activity performed by the user. For example, when a user performs voice communication or video communication, the current operation of the user may be affected if the terminal device is used to provide voice prompt or picture prompt, and this may be ineffective in adjusting the user emotion. Therefore, in this case, the wearable device may be used to display the activity information, or the wearable device may be used to provide voice prompt or vibration prompt, or the like. For another example, when the user is in a condition of rock climbing, working at heights, or driving, it may be inconvenient for the user to view a screen, and this may be ineffective in adjusting the user emotion if a manner of displaying a picture, modifying a theme, or modifying a wallpaper is used. Therefore, a manner such as voice prompt, playing music, or vibration prompt may be used to remind the user.

Figure 7A:
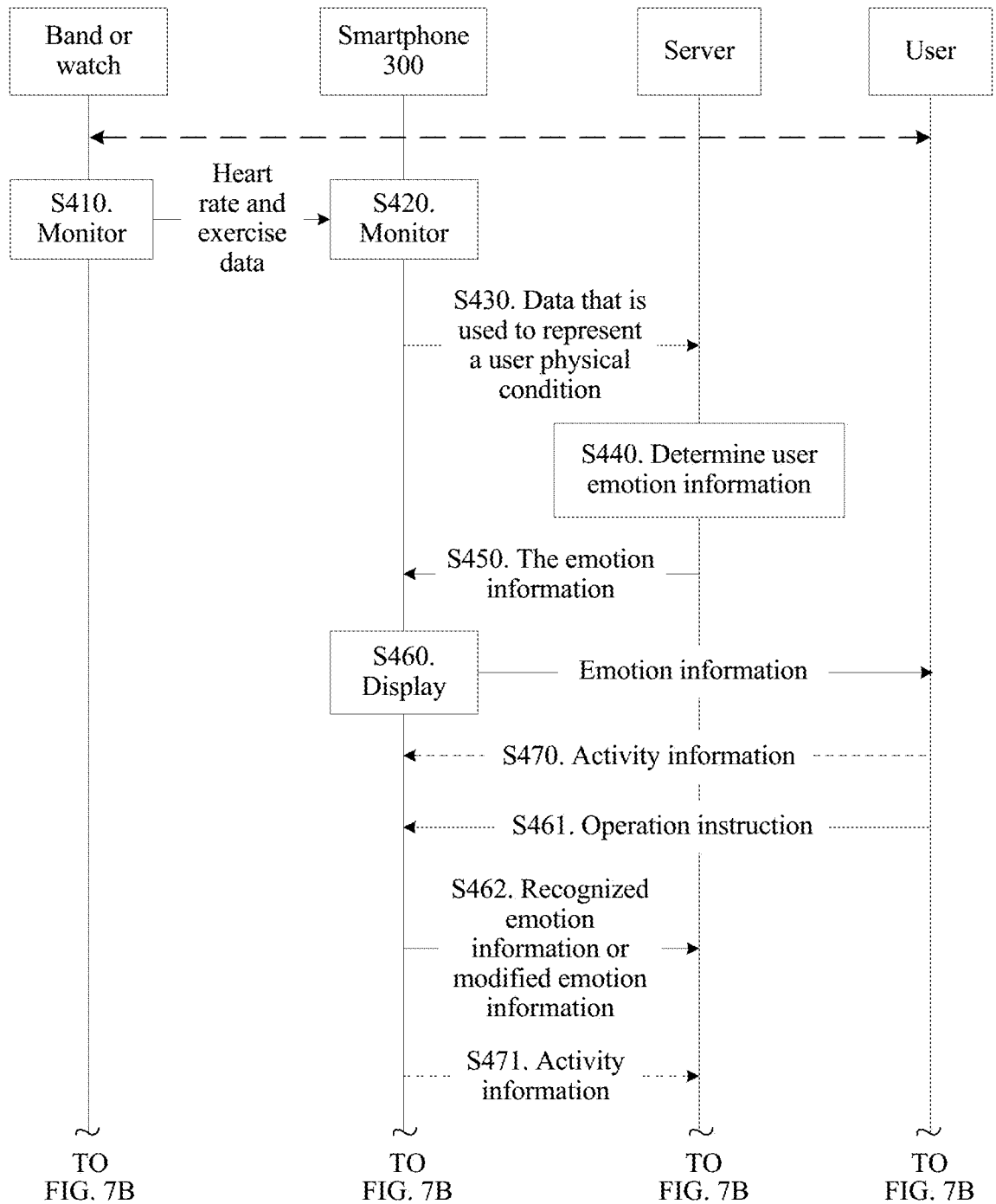
FIG. 7A and FIG. 7B are a schematic diagram of a method for adjusting a user emotion according to an embodiment of this application.
Figure 7B:
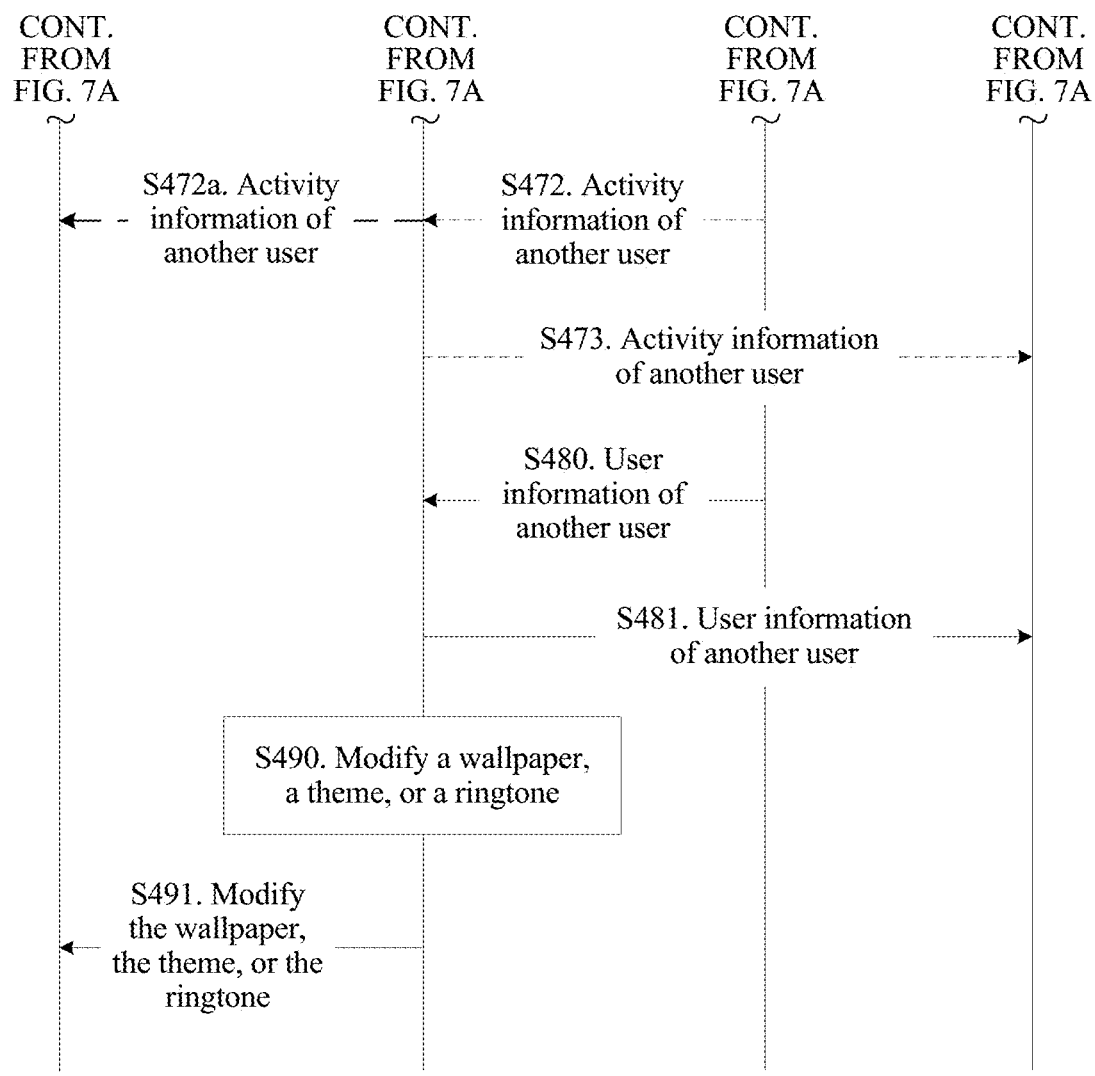

In this embodiment of this application, to save a storage space of the smartphone 300, the user emotion information may be determined by the server side, and recommended information or information about another user that may interact with the user is sent to the terminal. Specifically, referring to FIG. 7A and FIG. 7B, FIG. 7A and FIG. 7B are a schematic diagram of another method for adjusting a user emotion according to an embodiment of this application. Descriptions same as that in the embodiments corresponding to FIG. 3 and FIG. 4 are not repeated in this embodiment of this application.

S410. When a user wears a band or a watch, the band or the watch monitors at least one parameter value of the user, and sends the at least one parameter value of the user to a smartphone 300 by using Bluetooth or infrared. For a specific monitoring condition of the band or the watch, refer to the embodiment corresponding to FIG. 3. Details are not described in this embodiment of this application again.

The at least one parameter value monitored by the band or the watch may include but is not limited to at least one of the following: a pulse intensity, a heart rate value, a blood pressure value, and a temperature.

S420. The smartphone 300 monitors the at least one parameter value of the user by using a built-in sensor.

The at least one parameter value monitored by the smartphone 300 may include but is not limited to at least one of the following: a voice volume, a voice frequency, a pressure value sensed by a screen pressure sensor, and user expression data obtained by using a camera to take photos of the user.

The at least one parameter value that is received by the smartphone 300 and that is sent by the band or the watch and at least one parameter value monitored by the smartphone 300 forms data of the user that is used to represent a user physical condition.

S430. The smartphone 300 sends data that is used to represent a user physical condition to a server.

S440. The server determines user emotion information based on the data that is used to represent the user physical condition. Specifically, the manner described in S430 and S440 may be used to determine the user emotion information.

S450. The server sends the user emotion information to the smartphone 300.

S460. The smartphone 300 displays the user emotion information to the user.

Optionally, S461. After the smartphone 300 displays the user emotion information to the user, the smartphone 300 receives an operation instruction triggered by the user, where the operation instruction is used to instruct the user to recognize the emotion information or modify the emotion data.

Certainly, the user may configure the smartphone 300 based on a condition of the user without triggering the display operation instruction.

S462. The smartphone 300 sends the emotion information recognized by the user or the modified emotion information to the server. Therefore, the server receives the emotion information that is sent by the smartphone 300 and that is recognized by the user. The server updates, based on the emotion information recognized by the user or the modified emotion information, and the data used to represent the user physical condition, a user parameter table corresponding to the user. For a specific manner, refer to the embodiment shown in FIG. 4.

Optionally, the method further includes the following steps.

Figure 8:
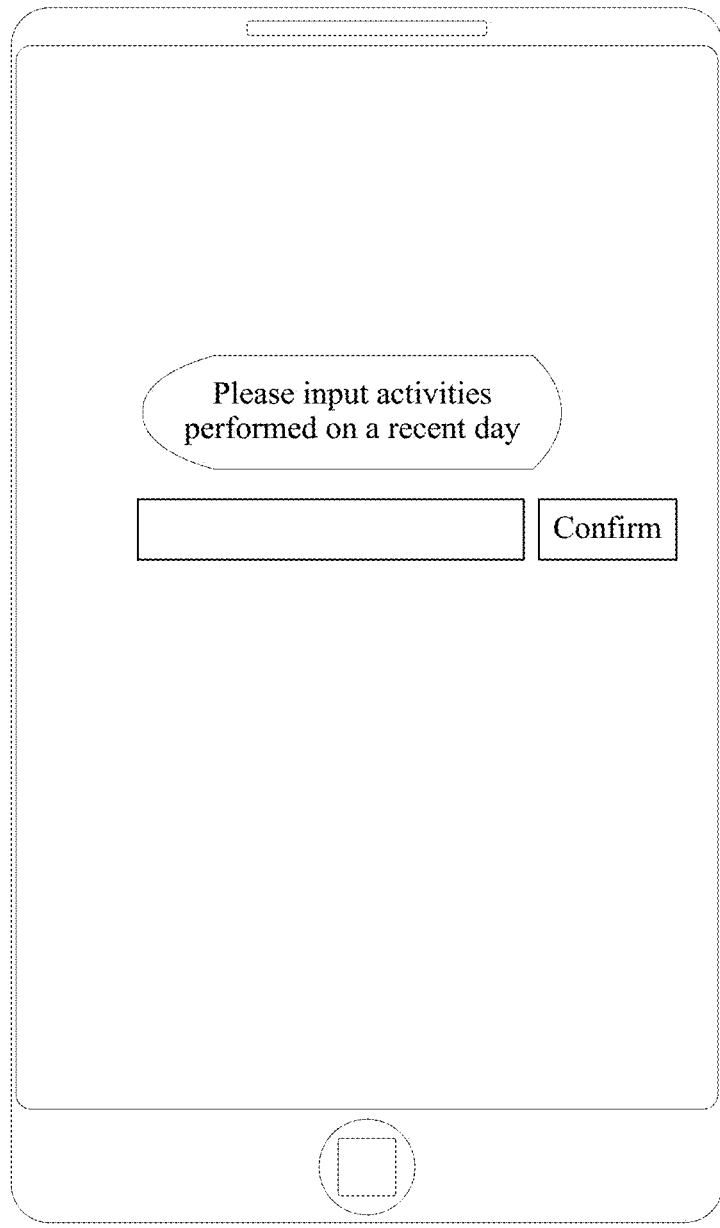
FIG. 8 is a schematic diagram of an interface for displaying a user activity input according to an embodiment of this application.

S470. After the smartphone 300 displays the emotion information to the user, each user (a user of the smartphone 300 is used as an example in FIG. 7A and FIG. 7B) may input an activity corresponding to a current time period or a time period displayed to the user such as reading, running, and listening to music. For example, on a display interface shown in FIG. 8, after inputting an activity in an input box shown in FIG. 8, the user of the smartphone 300 taps a "confirmation" icon, so that S471. After receiving a corresponding input instruction triggered by the user, the smartphone 300 sends activity information such as reading, running, and listening to music to the server. The input instruction carries current activity information of the user. Alternatively, after the smartphone 300 obtains data that is of the user corresponding to the smartphone 300 and that is used to represent the user physical condition, and before the data used to represent the user physical condition is sent to the server, instruction information is sent to the smartphone 300 to instruct the user to input an activity corresponding to the current time period, so that the smartphone 300 can obtain the activity of the current time period that is input by the user such as reading, running, and listening to music. Therefore, each terminal device sends obtained information such as reading, running, and listening to music that is input by a corresponding user to the server.

Based on this, after the server generates a user emotion value based on the user parameter table corresponding to the user and the data used to represent the user physical condition, the server determines a first emotion state corresponding to the user emotion value. Different emotion states are corresponding to different emotion value ranges, and the emotion state may include a normal emotion and an abnormal emotion, and may further include joyful, angry, and the like. The server obtains an activity performed by another user in a second emotion state, and recommends the activity to a user of the terminal device. Optionally, the user in the second emotion may be a user, whose distance to the user corresponding to the terminal device is less than or equal to a preset threshold, and the activity performed may be a proper activity performed recently such as a time period of a day or a week. For example, the first emotion state is an abnormal emotion, and the second emotion state is a normal emotion. If the user is in an abnormal emotion, for example, sad, the server may select an activity performed by a user in a joyful or happy state, and recommends the activity to the user corresponding to the terminal device. A configuration manner is not specifically limited in this embodiment of the present invention. In addition, the second emotion state is determined based on the configuration manner.

In addition, when recommending an emotion adjustment activity to the user, the terminal or the server may perform intelligent screening based on the activity of the user. For example, if an exercise amount of the user is large, for example, a quantity of steps is greater than a preset threshold, the exercise, or walking may be relatively ineffective in adjusting the user emotion. Therefore, other activities other than walking may be recommended first when an adjustment solution is recommended to the user.

S472. The server sends activity information of another user to the smartphone 300.

Optionally, S472a. The smartphone 300 may further send the activity information of another user to a band or a watch. When the band or the watch is connected to the server by using wireless connection, the activity information of another user may be sent to the band or the watch by the server.

S473. The smartphone 300 recommends the activity information of another user to the user of the smartphone 300.

Figure 9:
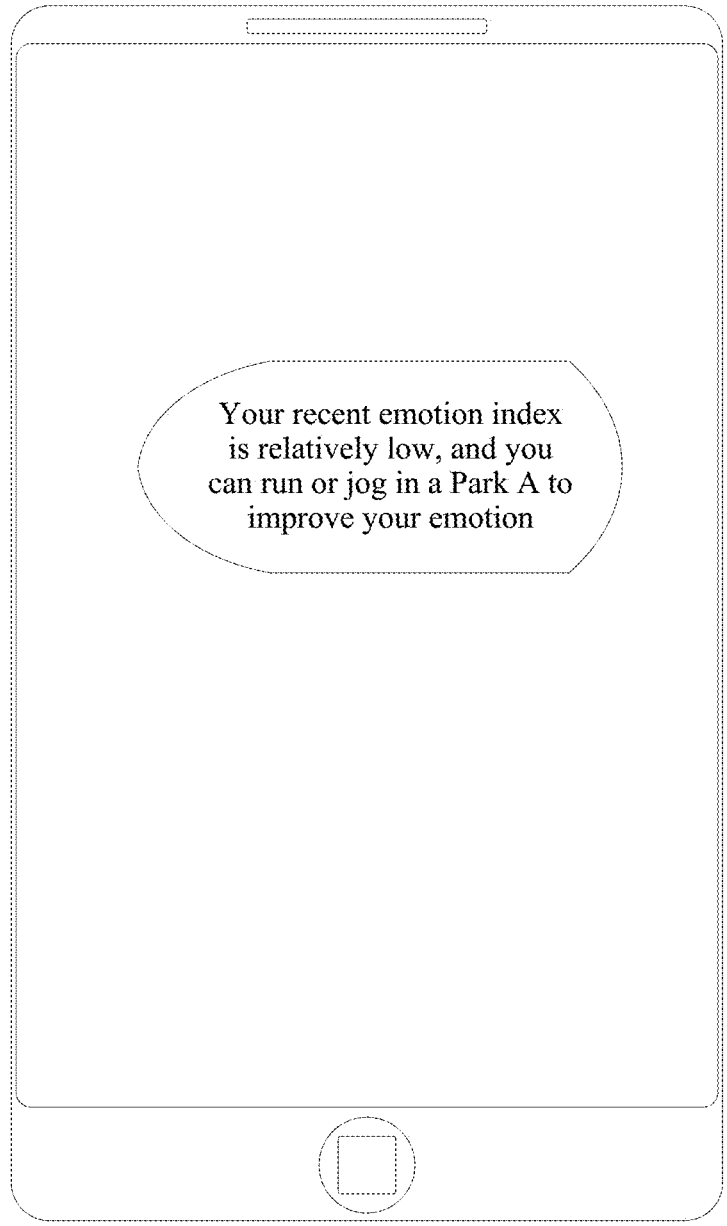
FIG. 9 is a schematic diagram of displaying activity information according to an embodiment of this application.

For example, when an emotion state of a current user is "sad", the server obtains a user in a "joyful" state, and a distance between the user in the "joyful" state and the user of the smartphone 300 is less than 3 kilometers. For example, a user Li Si meets the foregoing requirements after confirmation. Therefore, the server sends activity information corresponding to an activity performed by Li Si in a second set time period closest to a current time point to the smartphone 300. The smartphone 300 displays the activity information to the user, for example, display information received by the user is information displayed on a display interface shown in FIG. 9.

If the band or the watch provides a display function, the smartphone 300 may further send the activity information of another user to the band or the watch, so that the band or the watch displays the activity information of another user to the user.

In the foregoing implementation, the server provides corresponding advice to the user by using a data mining technology and by integrating user emotion information around the user and sensor data of the user. For example, if the user emotion is sad, advice is provided for the user by obtaining data of users whose emotions are happy around the user for integration (for example, if activities in a recent time period of users around the user that are screened by the server side and whose emotions are joyful are running in a park, the user is suggested to run in the park). In the prior art, only adjustment of a personal emotion is considered. However, in reality, emotion adjustment methods of other people, especially emotion adjustment methods of people around are usually helpful to a user. In the foregoing implementation, when the advice is provided, the emotion adjustment methods of the people around are considered by using the data mining technology. This increases efficiency of the adjustment.

In a possible implementation, after the user emotion information is displayed to the user in S470-S471, the user triggers the input activity information corresponding to the activity performed in the second set time period closest to the current time point. The smartphone 300 detects an input instruction triggered by the user of the smartphone 300, and the input instruction carries the activity information corresponding to the activity performed by the user in the second set time period closest to the current time point. The second set time period may be an hour, two hours, a day, or the like. This is not specifically limited in this embodiment of this application. For example, the second set time period is an hour, and if the current user inputs activity information at 10 past 2 o'clock, the server may search for users performing an activity between 1 o'clock and 2 o'clock.

The smartphone 300 sends the received activity information to the server, so that the server receives the activity information that is sent by the smartphone 300 and that is corresponding to the activity performed by the user in the second set time period closest to the current time point; then the server may determine the first emotion state corresponding to the user emotion value after the server generates the emotion value of the user of the smartphone 300 based on the user parameter table corresponding to the user and the user condition data, where different emotion states are corresponding to different emotion value ranges; and the server obtains user information of another user that is in the first emotion state and whose activity information is the same as the activity information of the user of the smartphone 300.

The method may further include the following steps.

S480. The server sends user information of another user to the smartphone 300.

S481. The smartphone 300 displays the user information to the user of the smartphone 300, so that the user of the smartphone 300 interacts with another user corresponding to the user information.

Figure 10A:
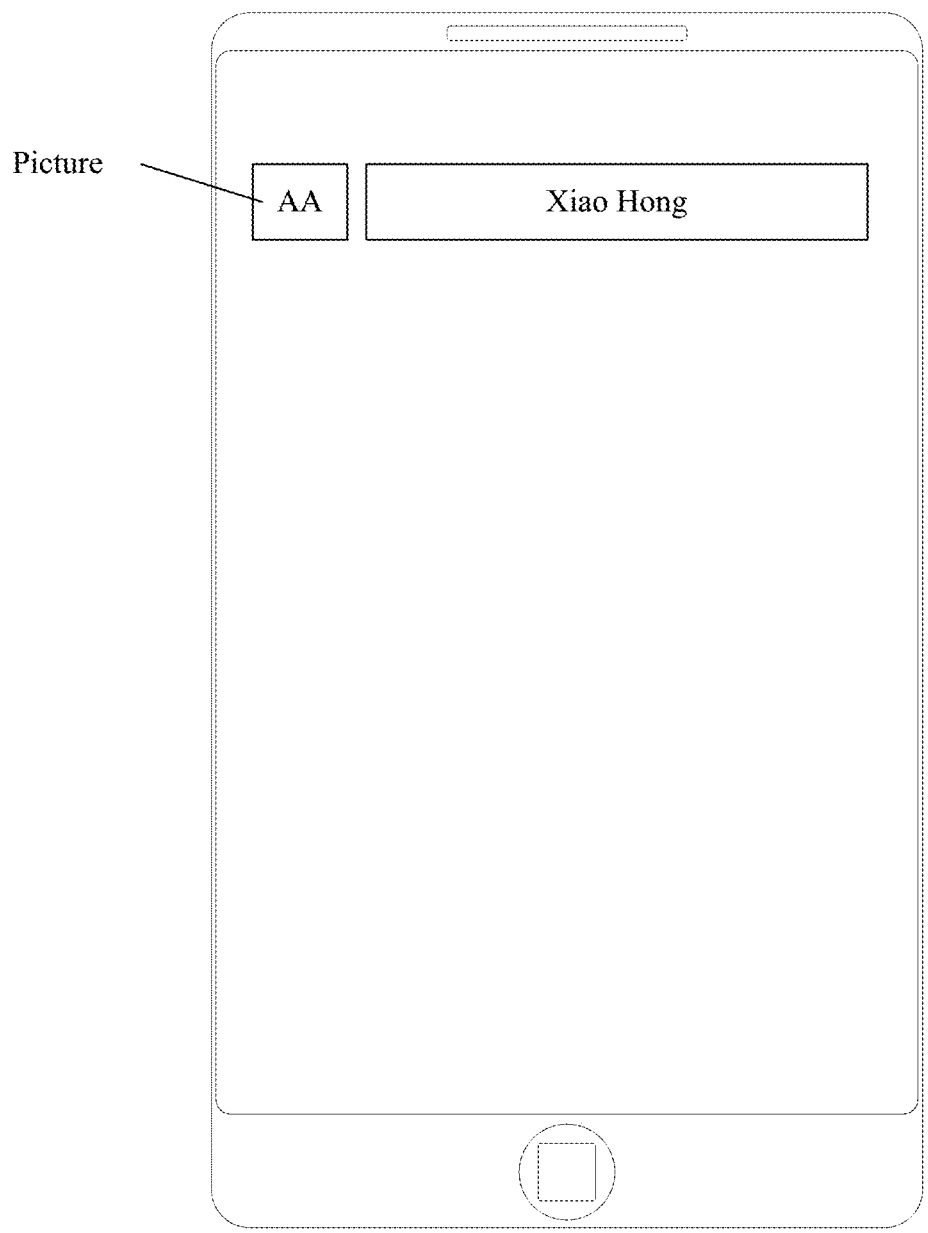
FIG. 10A is a schematic diagram of displaying information of another user according to an embodiment of this application.
Figure 10B:
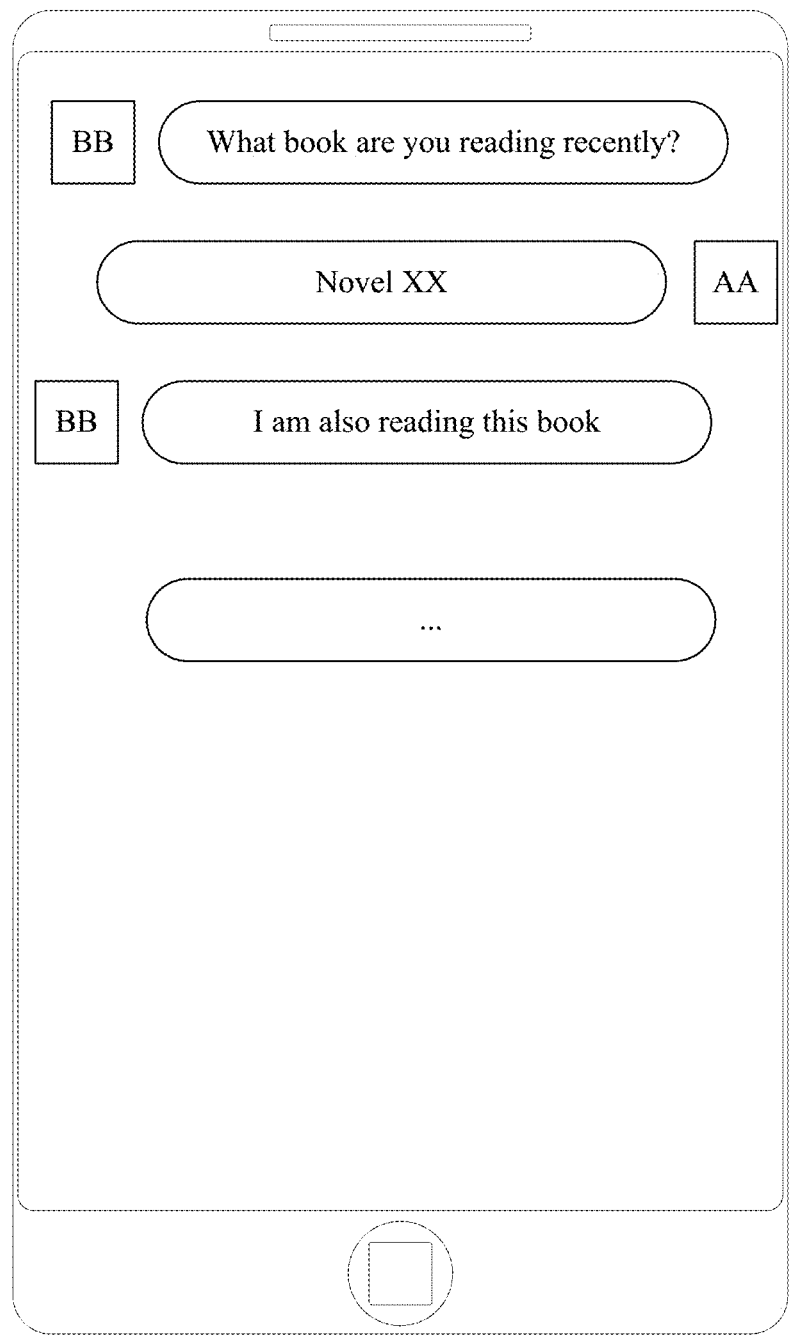
FIG. 10B is a schematic diagram of interaction between users according to an embodiment of this application.

After receiving the activity information of the user of the smartphone 300, the server searches for a matched user around the smartphone 300 and recommends the matched user to the user of the smartphone 300. For example, when the user inputs "reading", and a current emotion that is of the user of the smartphone 300 and that is determined by the server 120 is "sad", the server searches around for a user whose emotion is "sad" and whose current activity is reading and recommends the user to the user of the smartphone 300, so that the two users may interact with each other and improve the emotion. For example, if "Xiao Hong" is the user that meets the requirements: the emotion is "sad", and the current activity is reading, the smartphone 300 recommends information about Xiao Hong to the user of the smartphone 300. For example, on a display interface shown in FIG. 10A, a picture of the display interface shown in FIG. 10A may be used to represent a picture of Xiao Hong, and may be a profile picture AA specified by Xiao Hong. This is not specifically limited in this embodiment of this application. The user of the smartphone 300 may interact with Xiao Hong by tapping a "Xiao Hong" icon. For example, as shown in FIG. 10B, "BB" in FIG. 10B is used to represent the user of the smartphone 300.

Optionally, the method may further include the following steps.

S490. After obtaining the user emotion information sent by the server, the smartphone 300 may further perform an operation that is corresponding to the emotion information and that is used to adjust the user emotion. For example, the smartphone 300 displays the advice for the user to the user, for example, recommending a wallpaper, a theme, or a ringtone that may be modified to the user; or directly performing an operation of modifying a display wallpaper, a theme, a ringtone of the smartphone 300, or the like, or an operation of modifying an announcement, playing the music, or the like. In FIG. 7A and FIG. 7B, modifying the display wallpaper, the theme, or the ringtone of the smartphone 300 is used as an example.

S491. The smartphone 300 updates a theme, a wallpaper, an announcement, or the like of a device such as a band or a watch. Alternatively, the smartphone 300 may update an announcement or to-be-played music.

Figure 11:
FIG. 11 is a schematic diagram of displaying an emotion state on a wearable device according to an embodiment of this application.

For example, if current user emotion information of the smartphone 300 is "sad", the smartphone 300 modifies a wallpaper of the band or the watch by using infrared or Bluetooth, as shown in FIG. 11.

Figure 12:
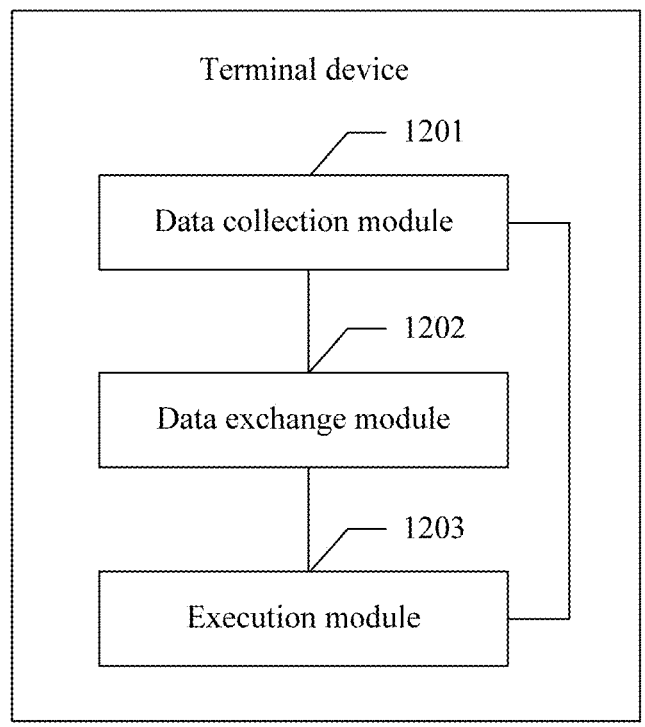
FIG. 12 is a schematic diagram of an apparatus for adjusting a user emotion according to an embodiment of this application.

Base on a same invention conception as that of the method embodiment, an embodiment of this application further provides an apparatus for adjusting a user emotion. The apparatus may be specifically implemented by a processor 320 in a smartphone 300. As shown in FIG. 12, the apparatus may include: a data collection module 1201, configured to obtain data that is used to represent a user physical condition, where the data includes first data, and the first data is at least one parameter value detected for the user by a wearable device connected to the terminal device; a data exchange module 1202, configured to obtain emotion information determined based on the data; and an execution module 1203, configured to perform an operation that is corresponding to the emotion information and that is used to adjust the user emotion.

In a possible implementation, the data that is obtained by the data collection module 1201 and that is used to represent the user physical condition further includes second data, and the second data is at least one parameter value of the user detected by the terminal device; and the data exchange module 1202 is specifically configured to obtain emotion information determined based on the first data and the second data.

In a possible implementation, the data exchange module 1202 is specifically configured to: determine the emotion information based on a parameter value of each parameter in the data and a corresponding weight.

In a possible implementation, the data exchange module 1202 is further configured to: send the obtained data to a server, and receive the emotion information returned by the server based on the data.

In a possible implementation, the execution module 1203 is specifically configured to: notify the user of a current emotion state of the user.

In a possible implementation, the execution module 1203 is specifically configured to: notify the user of the current emotion state of the user by using a voice or interface display; or send the emotion state to the wearable device, and notify the user of the current emotion state of the user by using the wearable device.

In a possible implementation, the execution module 1203 is specifically configured to: recommend activity information or interaction information that is used for adjusting emotion to the user; where the interaction information is used to perform interaction with another user.

In a possible implementation, the first data includes at least one of the following parameter values: a heart rate value, a blood pressure value, and a pulse intensity.

In a possible implementation, the second data includes at least one of the following parameter values: a voice rate, a voice intensity, a screen pressing intensity, and a facial expression.

In a possible implementation, the data exchange module 1202 is further configured to: after the execution module 1203 notifies the user of the current emotion state of the user, receive an operation instruction triggered by the user, and send the emotion information recognized by the user or modified emotion information to the server, where the operation instruction is used to instruct the user to recognize the emotion information or modify the emotion information.

Module division in this embodiment of this application is an example, is merely logical function division, and may be other division in actual implementation. In addition, function modules in embodiments of this application may be integrated into one processor, or each of the modules may exist alone physically, or two or more modules are integrated into one module. The integrated module may be implemented in a form of hardware, or may be implemented in a form of a software function module.

When the hardware is used for implementation, for hardware implementation of the terminal, refer to FIG. 2A and related description.

A transceiver is configured to receive first data sent by a wearable device connected to the terminal device, where the first data is at least one parameter value detected by the wearable device for the user; and a processor 320 is configured to: obtain data that is used to represent a user physical condition, where the data includes the first data received by the transceiver; obtain emotion information determined based on the data; and perform an operation that is corresponding to the emotion information and that is used to adjust the user emotion.

In a possible design, the data that is used to represent the user physical condition further includes second data, and the apparatus further includes: at least one sensor 370, configured to detect the second data that is used to represent the user physical condition, where the second data includes at least one parameter value; where when obtaining emotion information determined based on the data, the processor 320 is specifically configured to obtain emotion information determined based on the first data and the second data.

In a possible design, when obtaining the emotion information determined based on the data, the processor 320 is specifically configured to: determine the emotion information based on a parameter value of each parameter in the data and a corresponding weight.

In a possible design, the transceiver is further configured to: send the data obtained by the processor 320 to a server, and receive the emotion information returned by the server based on the data.

In a possible design, when performing the operation that is corresponding to the emotion information and that is used to adjust the user emotion, the processor 320 is specifically configured to: notify the user of a current emotion state of the user.

In a possible design, the apparatus may further include: a loudspeaker 390, configured to provide voice prompt; where the processor 320 is specifically configured to notify the user of the current emotion state of the user by using a voice given by the loudspeaker 390.

In a possible design, the apparatus may further include: a display device 310, configured to display prompt information; where the processor 320 is specifically configured to notify the user of the current emotion state of the user by using a display interface of the display device 310.

In a possible design, the transceiver is further configured to send the emotion state to the wearable device, so that the wearable device notifies the user of the current emotion state of the user.

In a possible design, the processor 320 is further configured to recommend, by using the display device 330, activity information or interaction information that is used for adjusting emotion to the user; where the interaction information is used to perform interaction with another user.

The first data includes at least one of the following parameter values: a heart rate value, a blood pressure value, and a pulse intensity. The second data includes at least one of the following parameter values: a voice rate, a voice intensity, a screen pressing intensity, and a facial expression.

The at least one sensor 370 includes at least one of the following: a voice receiver, configured to detect the voice rate and/or detect the voice intensity; a pressure sensor, configured to detect the screen pressing intensity; and an image sensor, configured for the facial expression.

In a possible implementation, the transceiver is further configured to: after the processor 320 notifies the user of the current emotion state of the user, receive an operation instruction triggered by the user, and send the emotion information recognized by the user or modified emotion information to the server, where the operation instruction is used to instruct the user to recognize the emotion information or modify the emotion information.

Figure 13:
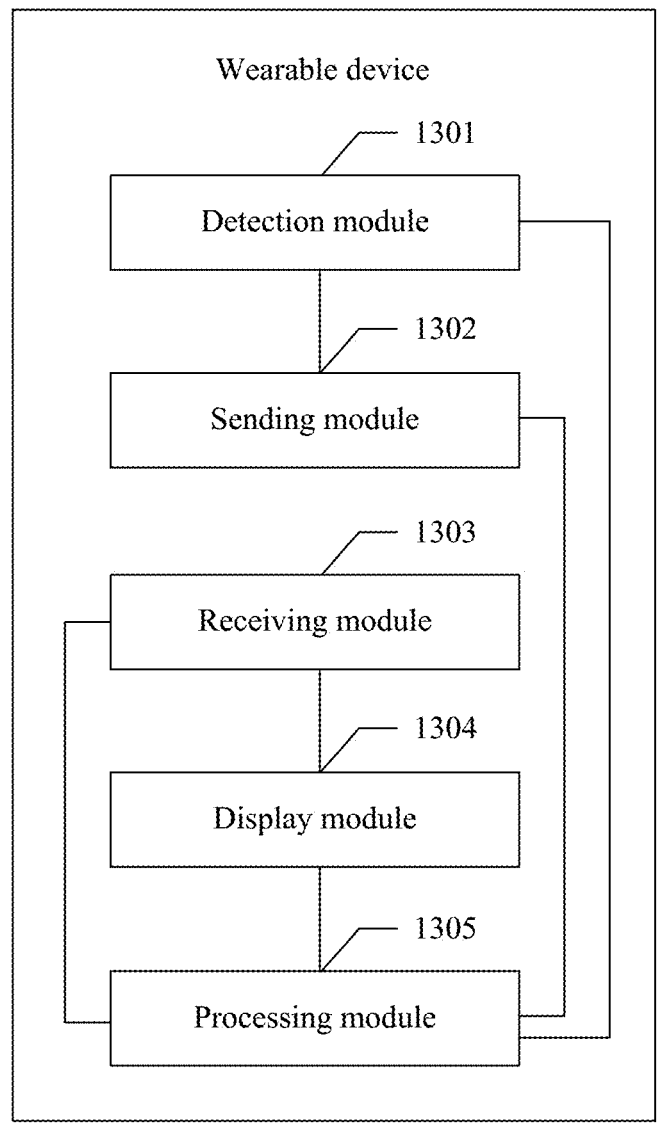
FIG. 13 is a schematic diagram of another apparatus for adjusting a user emotion according to an embodiment of this application.

Base on a same invention conception as that of the method embodiment, an embodiment of this application further provides an apparatus for adjusting a user emotion, and the apparatus is applied to a wearable device. As shown in FIG. 13, the apparatus includes: a detection module 1301, configured to detect at least one parameter value that is used to represent a user physical condition; and a sending module 1302, configured to send the at least one parameter value to a terminal device connected to the wearable device, so that the terminal device performs an emotion adjustment operation for the user based on the at least one parameter value.

In a possible implementation, the apparatus may further include: a receiving module 1303, configured to receive activity information that is sent by the terminal device and that is to be recommended to the user; and a display module 1304, configured to display the activity information.

In a possible implementation, the receiving module 1303 is configured to receive an instruction that is used for updating a theme, updating a wallpaper, updating an announcement, updating a ringtone, or playing the music and that is sent by the terminal device; and a processing module 1305, configured to: update, based on the instruction, the theme, the wallpaper, the announcement, or the ringtone, or play the music.

Module division in this embodiment of this application is an example, is merely logical function division, and may be other division in actual implementation. In addition, function modules in embodiments of this application may be integrated into one processor, or each of the modules may exist alone physically, or two or more modules are integrated into one module. The integrated module may be implemented in a form of hardware, or may be implemented in a form of a software function module.

When the hardware is used for implementation, for hardware implementation of the wearable device, refer to FIG. 2B and related description.

At least one sensor 302a is configured to detect at least one parameter value that is used to represent a user physical condition; and a transceiver 301a, configured to send the at least one parameter value to the terminal device, so that the terminal device performs an emotion adjustment operation for the user based on the at least one parameter value.

In a possible implementation, the transceiver 301a is further configured to receive activity information that is sent by the terminal device and that is to be recommended to the user; and a display device 303a is configured to display the activity information.

In a possible implementation, the transceiver 301a is further configured to receive an instruction that is used for updating a theme, updating a wallpaper, updating an announcement, updating a ringtone, or playing the music and that is sent by the terminal device; and the display device 303a is further configured to display the wallpaper or the theme; the apparatus further includes a processor 304a, configured to: update, based on the instruction, the theme, the wallpaper, the announcement, or the ringtone, or play the music; the display device 303a is further configured to display the wallpaper or the theme that is updated by the processor 304a; and the apparatus further includes a loudspeaker 305a, configured to: give the announcement updated by the processor 304a, or give the ringtone updated by the processor 304a, or play the music.

In the method for adjusting a user emotion in a convenient and effective way that is provided in the foregoing solution, a dedicated device, for example, a finger sensor, is not needed. Instead, the wearable device is used to obtain, in real time, the parameter value that is used to represent the user physical condition, and send the parameter value to the terminal device. The terminal device determines the user emotion based on the parameter value, and then performs the operation that is used to adjust the user emotion. This provides relatively high convenience for the user and delivers high real-timeness and operability.

A person skilled in the art should understand that the embodiments of this application may be provided as a method, a system, or a computer program product. Therefore, this application may use a form of hardware only embodiments, software only embodiments, or embodiments with a combination of software and hardware. In addition, this application may use a form of a computer program product that is implemented on one or more computer-usable storage media (including but not limited to a disk memory, a CD-ROM, an optical memory, and the like) that include computer usable program code.

This application is described with reference to the flowcharts and/or block diagrams of the method, the device (system), and the computer program product according to the embodiments of this application. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner, so that the instructions stored in the computer readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Obviously, a person skilled in the art can make various modifications and variations to the embodiments of this application without departing from the spirit and scope of the embodiments of this application. This application is intended to cover these modifications and variations provided that they fall within the scope of protection defined by the following claims and their equivalent technologies.

What is claimed is:

1. A method for adjusting a user's emotion performed by an electronic device, the method comprising:
    obtaining, by the electronic device, data representing a physical condition of the user, wherein the data comprises first data, the first data is at least one parameter value of the user detected by a wearable device worn by the user, and the wearable device is configured to communicate with the electronic device;
    obtaining, by the electronic device, emotion information determined based on the data and a parameter table specific to the user, wherein the parameter table is stored on the electronic device or a server configured to communicate with the electronic device; and
    recommending, by the electronic device, another user's emotion information in a past time period to the user using a voice prompt or a display interface, wherein a distance between the another user and the user is less than or equal to a preset threshold, and the another user's emotion information and the emotion information of the user are different; or
    recommending, by the electronic device, another user to the user using a voice prompt or a display interface, wherein the distance between the another user and the user is less than or equal to a preset threshold, and the another user's emotion information and current activity respectively are the same as the emotion information and current activity of the user.

2. The method according to claim 1, wherein:
    the data further comprises second data, and the second data is at least one parameter value of the user detected by the electronic device and is different from the first data; and
    obtaining, by the electronic device, the emotion information determined based on the data and the parameter table specific to the user comprises obtaining, by the electronic device, emotion information determined based on the first data, the second data, and the parameter table.

3. The method according to claim 2, wherein:
    the parameter table is stored on the server configured to communicate with the electronic device; and
    obtaining, by the electronic device, the emotion information determined based on the data and the parameter table specific to the user comprises:
        sending, by the electronic device, the data to the server; and
        receiving the emotion information returned by the server based on the data and the parameter table.

4. The method according to claim 3, wherein the method further comprises:
    notifying, by the electronic device, the user of a current emotion state of the user.

5. The method according to claim 4, wherein notifying, by the electronic device, the user of the current emotion state of the user comprises:
    notifying, by the electronic device, the user of the current emotion state of the user using a voice prompt or a display interface; or
    sending, by the electronic device, the current emotion state of the user to the wearable device, to cause the wearable device to notify the user of the current emotion state of the user.

6. The method according to claim 4, wherein the method further comprises, after notifying, by the electronic device, the user of the current emotion state of the user:
    receiving, by the electronic device, an operation instruction triggered by the user, wherein the operation instruction instructs the user to recognize the emotion information or modify the emotion information; and
    sending, by the electronic device to the server, the emotion information recognized by the user or the modified emotion information.

7. The method according to claim 3, wherein the method further comprises:

recommending, by the electronic device, activity information for adjusting the emotion of the user.

8. The method according to claim 7, wherein the first data comprises at least one of the following parameter values: a heart rate value, a blood pressure value, and a pulse intensity.

9. The method according to claim 8, wherein the second data comprises at least one of the following parameter values: a voice rate, a voice intensity, a screen pressing intensity, and a facial expression.

10. The method according to claim 1, wherein obtaining, by the electronic device, the emotion information determined based on the data and the parameter table comprises:
   determining the at least one parameter value based on the first data;
   determining at least one weight respectively corresponding to the at least one parameter based on the at least one parameter value and the parameter table; and
   determining, by the electronic device, the emotion information based on the at least one parameter value and the at least one weight respectively corresponding to the at least one parameter value.

11. A system comprising:
   an electronic device;
   a wearable device;
   wherein the electronic device is configured to communicate with the wearable device using a short range wireless communication protocol;
   wherein the wearable device comprises at least one first processor and a first memory coupled to the at least one first processor, the first memory storing first programming instructions that, when executed by the at least one first processor, cause the wearable device to:
      detect first data represented by a physical condition of a user who wears the wearable device;
      send the first data to the electronic device, the electronic device also associated with the user;
      receive, from the electronic device, an instruction for updating a theme, updating a wallpaper, updating an announcement, updating a ringtone, or playing music; and
      in response to receiving the instruction, update the theme, update the wallpaper, update the announcement, update the ringtone, or play the music; and
   wherein the electronic device comprises at least one second processor and a second memory coupled to the at least one second processor, the second memory storing second programming instructions that, when executed by the at least one second processor, cause the electronic device to:
      receive the first data from the wearable device;
      obtain emotion information determined based on the first data and a parameter table specific to the user, wherein the parameter table is stored on the electronic device or a server configured to communicate with the electronic device;
      output the emotion information;
      obtain a user input verifying the emotion information and updating the parameter table based on the emotion information; and
      recommend another user's emotion information in a past time period to the user using a voice prompt or a display interface, wherein a distance between the another user and the user is less than or equal to a preset threshold, and the another user's emotion information and the emotion information of the user are different; or
      recommend another user to the user using a voice prompt or a display interface, wherein the distance between the another user and the user is less than or equal to a preset threshold, and the another user's emotion information and current activity respectively are the same as the emotion information and current activity of the user;
      generate an instruction for updating a theme, updating a wallpaper, updating an announcement, updating a ringtone, or playing music; and
      send the instruction to the wearable device.

12. The system according to claim 11, wherein the first data comprises at least one of the following parameter values: a heart rate value, a blood pressure value, and a pulse intensity.

13. The system according to claim 12, wherein the second programming instructions further cause the electronic device to:
   detect second data that is different from the first data and comprises at least one parameter value of the user; and
   obtain the emotion information determined based on the first data and a parameter table specific to the user by performing operations that comprise:
      obtaining the emotion information determined based on the first data, the second data, and the parameter table.

14. The system according to claim 13, wherein the second programming instructions further cause the electronic device to:
   notify the user of a current emotion state of the user.

15. The system according to claim 14, wherein notify the user of the current emotion state of the user comprises:
   notify a current emotion state of the user using a voice prompt or a display interface; or
   send a current emotion state of the user to the wearable device, to cause the wearable device to notify the user of the current emotion state of the user.

16. The system according to claim 13, wherein the second data comprises at least one of the following parameter values: a voice rate, a voice intensity, a screen pressing intensity, and a facial expression.

17. The system according to claim 12, wherein the second programming instructions further cause the electronic device to:
   send the first data to a server; and
   receive the emotion information returned by the server based on the first data and the parameter table.

18. The system according to claim 17, wherein the second programming instructions further cause the electronic device to:
   recommend activity information for adjusting the emotion of the user; and
   display the activity information.

19. The system according to claim 17, wherein the second programming instructions further cause the electronic device to:
   receive an operation instruction triggered by the user, wherein the operation instruction instructs the user to recognize the emotion information or modify the emotion information; and
   send to the server the emotion information recognized by the user or the modified emotion information.

20. An electronic device comprising:
   at least one processor; and a memory coupled to the at least one processor, the memory storing programming instructions that, when executed by the at least one processor, cause the electronic device to:

receive first data from a wearable device that is configured to communicate with the electronic device;

obtain emotion information determined based on the first data and a parameter table specific to a user, wherein the parameter table is stored on the electronic device or a server configured to communicate with the electronic device;

output the emotion information;

obtain a user input verifying the emotion information and updating the parameter table based on the emotion information;

recommend another user's emotion information in a past time period to the user using a voice prompt or a display interface, wherein a distance between the another user and the user is less than or equal to a preset threshold, and the another user's emotion information and the emotion information of the user are different; or recommend another user to the user using a voice prompt or a display interface, wherein the distance between the another user and the user is less than or equal to a preset threshold, and the another user's emotion information and current activity are respectively the same as the emotion information and current activity of the user;

generate an instruction for updating a theme, updating a wallpaper, updating an announcement, updating a ringtone, or playing music; and send the instruction to the wearable device.

* * * * *